(12) United States Patent
Moore

(10) Patent No.: US 12,290,648 B2
(45) Date of Patent: May 6, 2025

(54) NEEDLE GUIDING SYSTEM

(71) Applicant: Trenton W. Moore, Sarasota, FL (US)

(72) Inventor: Trenton W. Moore, Sarasota, FL (US)

(73) Assignee: Trenton W. Moore, Sarasota, FL (US)

( * ) Notice: Subject to any disclaimer, the term of this patent is extended or adjusted under 35 U.S.C. 154(b) by 300 days.

(21) Appl. No.: 17/148,757

(22) Filed: Jan. 14, 2021

(65) Prior Publication Data

US 2021/0213256 A1 Jul. 15, 2021

Related U.S. Application Data

(60) Provisional application No. 62/960,888, filed on Jan. 14, 2020.

(51) Int. Cl.
*A61M 25/06* (2006.01)
*A61M 5/158* (2006.01)
*A61M 5/168* (2006.01)

(52) U.S. Cl.
CPC ................................ *A61M 25/065* (2013.01)

(58) Field of Classification Search
CPC .......... A61M 25/065; A61M 2205/583; A61M 2209/088; A61M 5/1684; A61M 5/427; A61M 5/16854; A61M 2005/1585; A61M 2005/1586
See application file for complete search history.

(56) References Cited

U.S. PATENT DOCUMENTS

| | | | | |
|---|---|---|---|---|
| 4,966,589 | A | * 10/1990 | Kaufman | .......... A61M 25/0631 604/116 |
| 6,283,942 | B1 | * 9/2001 | Staehlin | .............. A61M 5/3287 604/116 |
| 2013/0338480 | A1 | * 12/2013 | Hann | ..................... A61M 5/158 600/409 |
| 2014/0188002 | A1 | * 7/2014 | Close | ............... A61B 5/150992 600/581 |
| 2019/0021953 | A1 | * 1/2019 | Ravussin | ............... A61J 1/2093 |

* cited by examiner

*Primary Examiner* — Bhisma Mehta
*Assistant Examiner* — Hamza A Darb
(74) *Attorney, Agent, or Firm* — K&L Gates LLP

(57) ABSTRACT

Needle guiding systems and methods for assembling and using the same are disclosed. The needle guiding systems can utilize a fluid bag, a compression sleeve, a guiding track, and a needle block assembly.

24 Claims, 18 Drawing Sheets

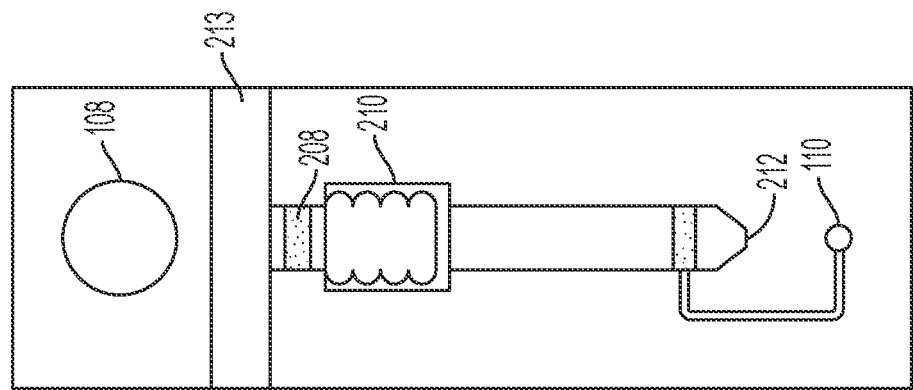
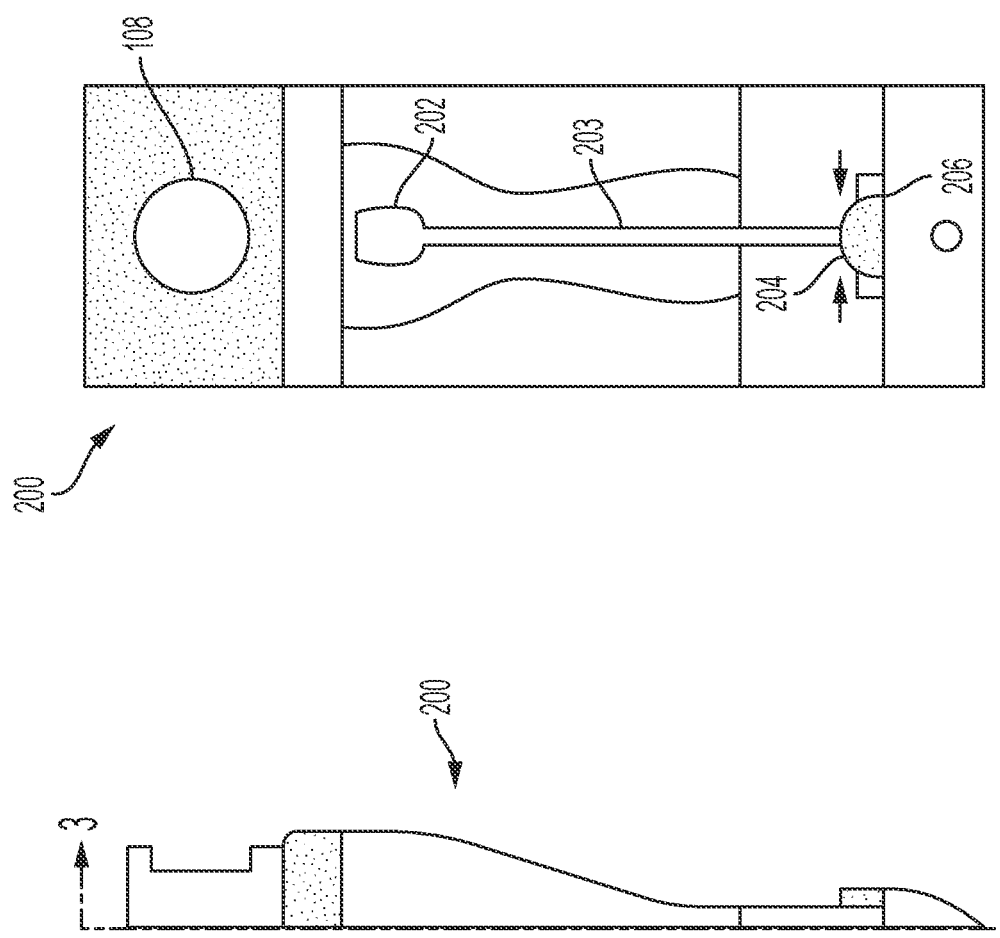

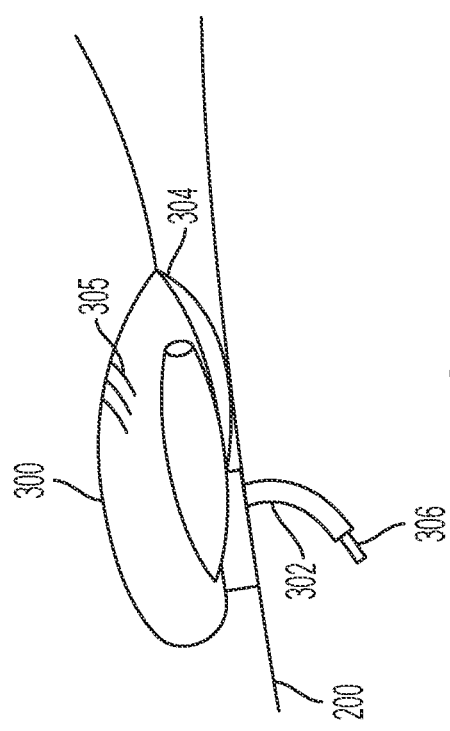
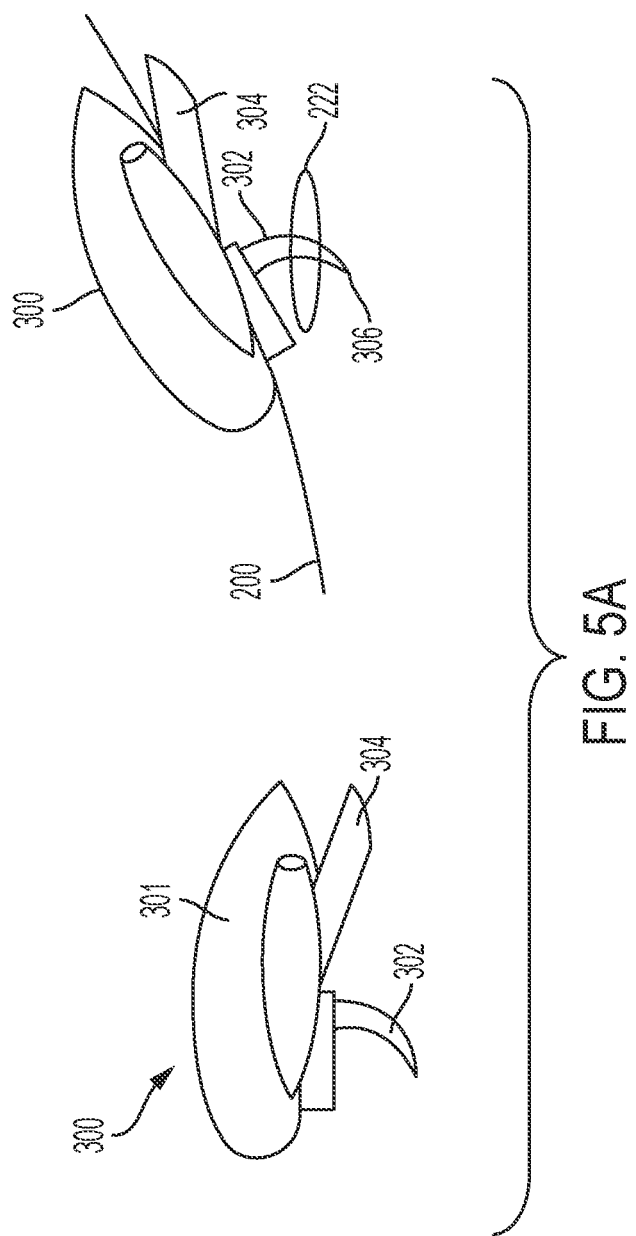

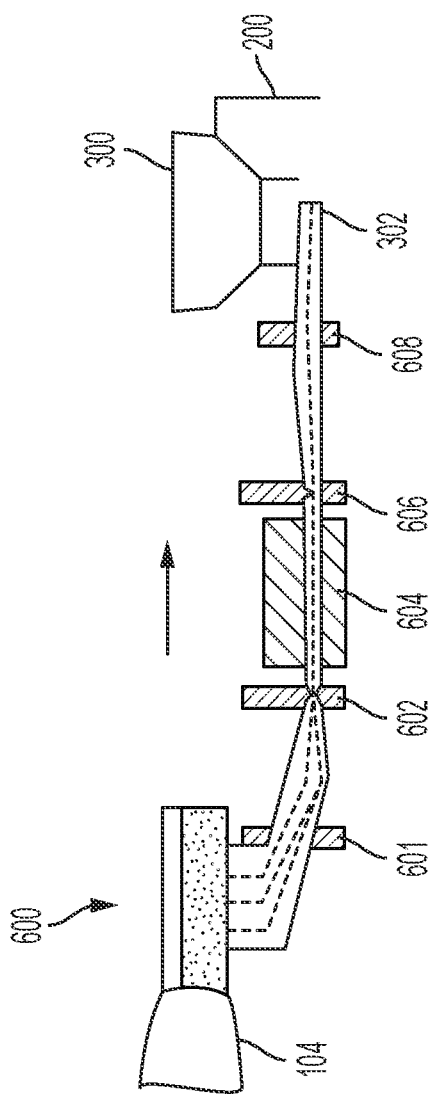
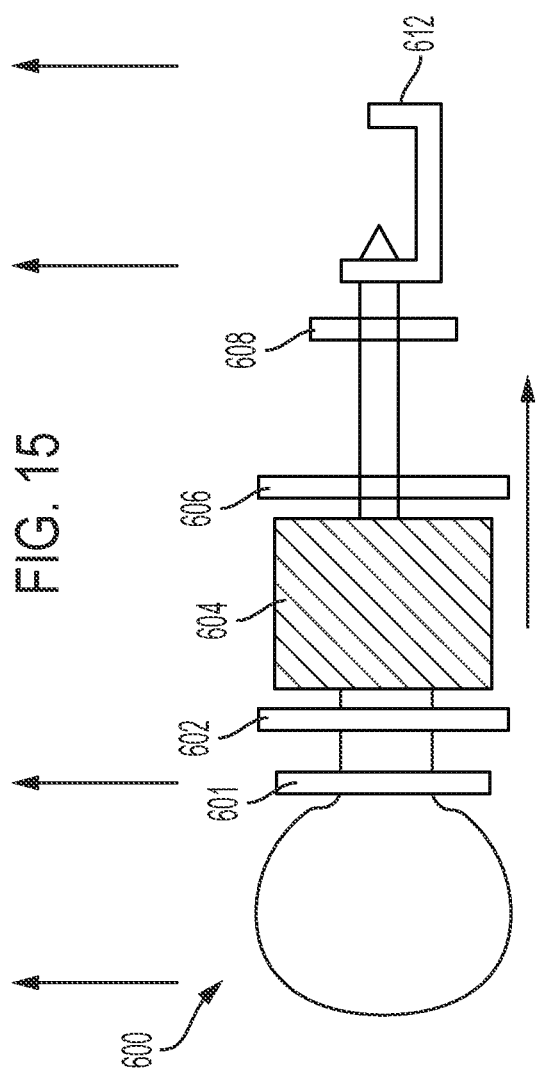
FIG. 15
FIG. 15A

NEEDLE GUIDING SYSTEM

CROSS-REFERENCE TO RELATED APPLICATION

This application claims the benefit of U.S. Provisional Patent Application Ser. No. 62/960,888, entitled NEEDLE GUIDING SYSTEM, filed Jan. 14, 2020, the entire disclosure of which is hereby incorporated by reference herein.

FIELD

The present disclosure relates to intravenous therapy systems and methods for using the same.

BACKGROUND

Intravenous therapy devices can be employed in various medical environments. Intravenous (IV) therapy is a medical treatment that delivers fluids directly into a vein by way of a catheter housed within a needle. IV therapy is often used for replacing fluid volume, correcting electrolyte imbalances, delivering medications, and completing blood transfusions. Because medications and fluid are introduced directly into the body's circulatory system, IV therapy is often the most efficient way to deliver medications and fluid replacement throughout the body.

SUMMARY

In one general aspect of the present invention, various systems for guiding a needle for IV fluid delivery are disclosed. The various systems described herein can include a compression sleeve, a fluid bag, and a needle insertion assembly having a guiding track and a needle block assembly, also referred to as a "tack" in some instances.

In another aspect of the present invention, a needle guiding system is disclosed. The needle guiding system includes a compression sleeve and a guiding track. The guiding track is configured to be attached to the compression sleeve and comprises a first end and a second end. The needle guiding system also includes a needle block assembly comprising a needle. The needle block assembly is configured to travel along the guiding track from the first end to the second end. The needle is configured to enter a vein at a predetermined position when the needle block assembly is seated in the second end of the guiding track.

In another aspect of the present invention, a method for inserting a needle into a vein is disclosed. The method includes applying a sleeve to a patient's arm. The sleeve comprises a guiding track and an insertion marker. The method also includes determining a needle insertion location. The insertion marker is configured to align with the needle insertion location. The method also includes attaching a fluid bag to the guiding track, wherein the attachment of the fluid bag opens a valve or port on the guiding track. The method also includes aligning a needle block assembly with the guiding track, wherein the needle block assembly comprises a needle and/or catheter. The needle block assembly is configured to travel from a starting point of the guiding track to an ending point of the guiding track, wherein the needle block assembly is locked into place once reaching the ending point, and wherein the needle is inserted into the patient's arm once the needle block assembly is locked into place at the ending point of the guiding track.

In another aspect of the present invention, a mobile intravenous therapy device is disclosed. The mobile intravenous therapy device includes a compression sleeve and a guiding track attached to the compression sleeve. The guiding track comprises a starting platform and an ending platform. The mobile intravenous therapy device also includes a fluid bag defining a fluid path threadably coupled to the guiding track, wherein the fluid bag comprises a medicament. The mobile intravenous therapy device also includes a needle assembly comprising a needle, wherein the needle assembly is configured to travel in the guiding track from the starting platform to the landing platform in order to insert the needle into a vein at a predetermined position once the needle assembly reaches the landing platform of the guiding track.

FIGURES

Features of various aspects are set forth with particularity in the appended claims. The described aspects, however, both as to organization and methods of operation, may be best understood by reference to the following description, taken in conjunction with the accompanying drawings in which:

FIG. 3 illustrates a cross-sectional plan view of a guiding track of the needle insertion system of FIG. 1 taken along plane 3-3 in FIG. 3A, according to at least one aspect of the present disclosure.

FIG. 3A illustrates a side view of the guiding track of FIG. 3, according to at least one aspect of the present disclosure.

FIG. 3B illustrates a top view of the guiding track of FIG. 3, according to at least one aspect of the present disclosure.

FIG. 5 illustrates a side view of a needle block assembly configured for use with the needle guiding system of FIGS. 1-4, according to at least one aspect of the present disclosure.

FIG. 5A illustrates side views of a needle block assembly configured for use with the needle guiding system illustrated in FIGS. 1-4, according to at least one aspect of the present disclosure.

FIG. 15 illustrates a side view of a sensor system, according to at least one aspect of the present disclosure.

FIG. 15A illustrates a top view of the sensor system of FIG. 15, according to at least one aspect of the present disclosure.

Corresponding reference characters indicate corresponding parts throughout the several views. The exemplifications set out herein illustrate various embodiments of the invention, in one form, and such exemplifications are not to be construed as limiting the scope of the invention in any manner.

DETAILED DESCRIPTION

Before explaining various aspects of a needle guiding system in detail, it should be noted that the illustrative examples are not limited in application or use to the details of construction and arrangement of parts illustrated in the accompanying drawings and description. The illustrative examples may be implemented or incorporated in other aspects, variations, and modifications, and may be practiced or carried out in various ways. Further, unless otherwise indicated, the terms and expressions employed herein have been chosen for the purpose of describing the illustrative examples for the convenience of the reader and are not for the purpose of limitation thereof. Also, it will be appreciated that one or more of the following-described aspects, expressions of aspects, and/or examples, can be combined with any one or more of the other following-described aspects, expressions of aspects, and/or examples.

Figure 1:
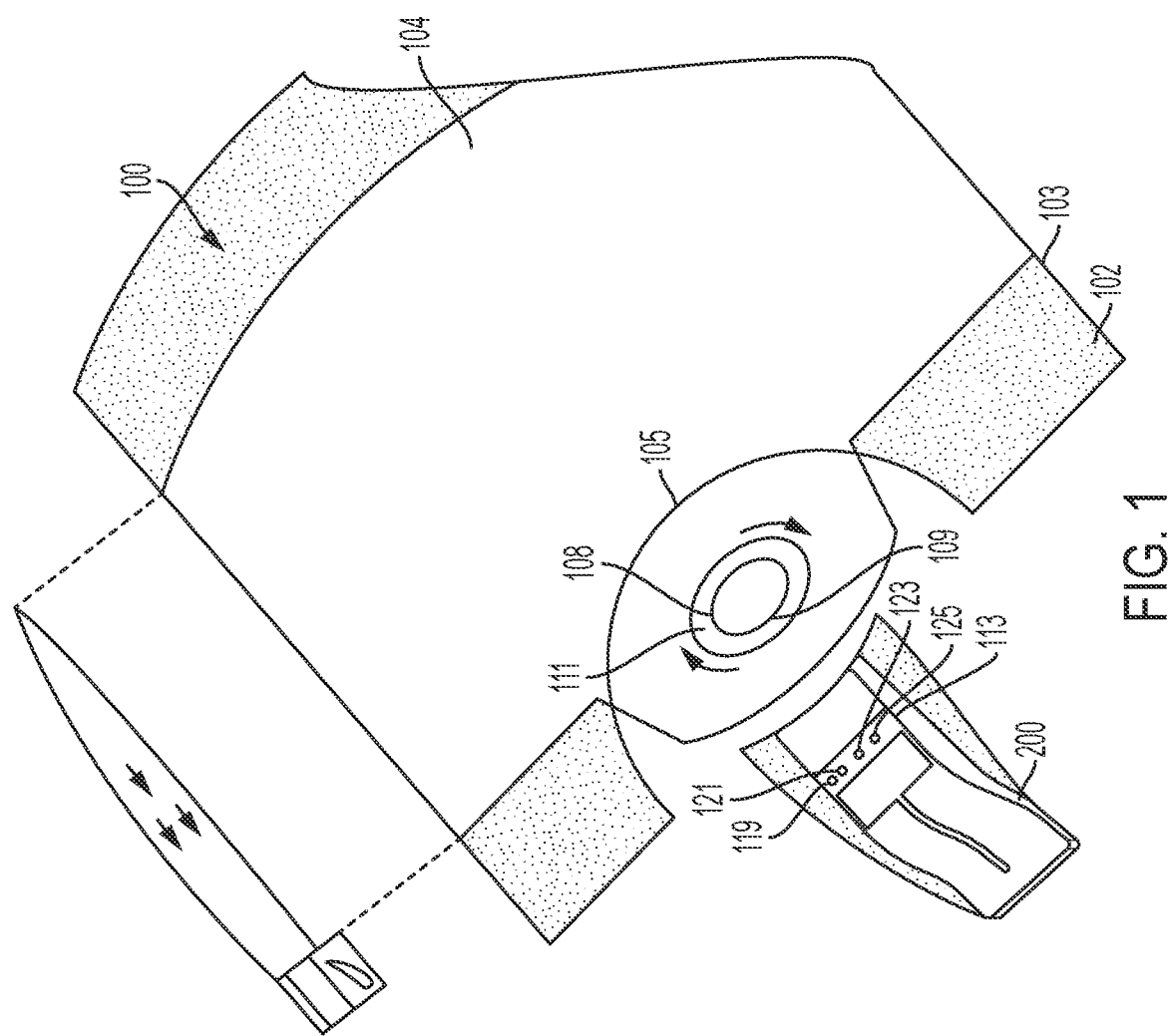
FIG. 1 illustrates an exploded perspective view of portions of a needle insertion system, according to at least one aspect of the present disclosure.

A needle guiding system according to various embodiments is depicted in FIG. 1. The needle guiding system 100 comprises a compression sleeve 102, which is configured to be attached to a patient's arm. Other embodiments contemplate attachment of the compression sleeve 102 at the wrist, shoulder, leg, or other portions of the body, for example. In some instances, the compression sleeve 102 comprises an ergonomic sleeve-like wearable accessory, which is configured to stay in place as a user operates the needle guiding system 100. The compression sleeve 102 includes a compression mechanism which serves as a tourniquet to establish blood flow. The compression sleeve 102 comprises a flexible fabric, which contours to a wearer's arm, for instance. The compression sleeve 102 can comprise an optional strap for additional compression or for additional securing purposes in some embodiments. The compression sleeve 102 comprises a hole 222 (see FIG. 5) on the inner side of the compression sleeve 102, which is configured to align with a predetermined needle insertion point, as will be discussed in greater detail below. In other instances, the compression sleeve 102 can include an insertion marker for aligning with the predetermined needle insertion point; however, the insertion marker may not be a hole. The insertion point on the patient's arm comprises a vein marker. The vein marker indicates to the user an appropriate location to align the hole 222 (or other insertion marker) of the compression sleeve 102. In many instances, the user of the needle guiding system 100 can determine the needle insertion point with vein-finding technology, such as infrared vein-finding technology and use any suitable vein marker after determining the needle insertion point. For example, infrared light can be utilized to illuminate a target, i.e. vein, within a patient.

Still referring primarily to FIG. 1, the needle guiding system 100 comprises a fluid bag 104 which is configured to be attached to a guiding track 200. The guiding track 200 is attached to the compression sleeve 102, as will be discussed in greater detail below. In other instances, the guiding track 200 can be glued, fastened, snapped, or otherwise securely attached to the compression sleeve 102. The compression sleeve 102 includes an encasement 103 for securing the fluid bag 104 in place on the compression sleeve 102 once the user attaches the fluid bag 104 to the guiding track 200. In some instances, the encasement 103 can comprise a mesh material. Other embodiments are envisioned where the compression sleeve 102 comprises a transparent plastic encasement for securing the fluid bag 104 in place, although any suitable material may be used for securing the fluid bag 104 to the compression sleeve 102. For example, in some instances, the compression sleeve 102 includes a flexible or moldable enclosure, which secures the fluid bag 104 in the compression sleeve 102. As another example, the compression sleeve 102 can comprise an elastic band to secure the fluid bag 104 thereto.

In some instances, the fluid bag 104 can be comprised of polyvinyl chloride (PVC) or any one of ethylene vinyl acetate, polypropylene, and/or copolyester ether, although the composition of the fluid bag 104 is not limited to these materials. The fluid bag 104 is configured to store a medicament therein. In some instances, the fluid bag 104 comprises a single medicament. In other instances, the fluid bag 104 includes a saline solution and a medicament.

A connector port 105 is defined in the guiding track 200 for securing the fluid bag 104 to the guiding track 200. As illustrated in FIG. 1, the connector port 105 of the guiding track 200 comprises a threaded attachment mechanism 109 for securing the fluid bag 104 to the guiding track 200. During a procedure, the fluid bag 104 remains fixed to the guiding track 200 and does not move with the needle insertion assembly. However, embodiments are envisioned where a smaller fluid bag is attached to the needle block assembly portion and travels with the needle block assembly along the guiding track 200. In still other instances, a fluid conduit can extend from the fluid bag 104, which can provide a fluid flow path for medicament(s) and/or saline. An end or outlet port of the fluid conduit may travel with the needle block assembly in such instances.

Figure 8:
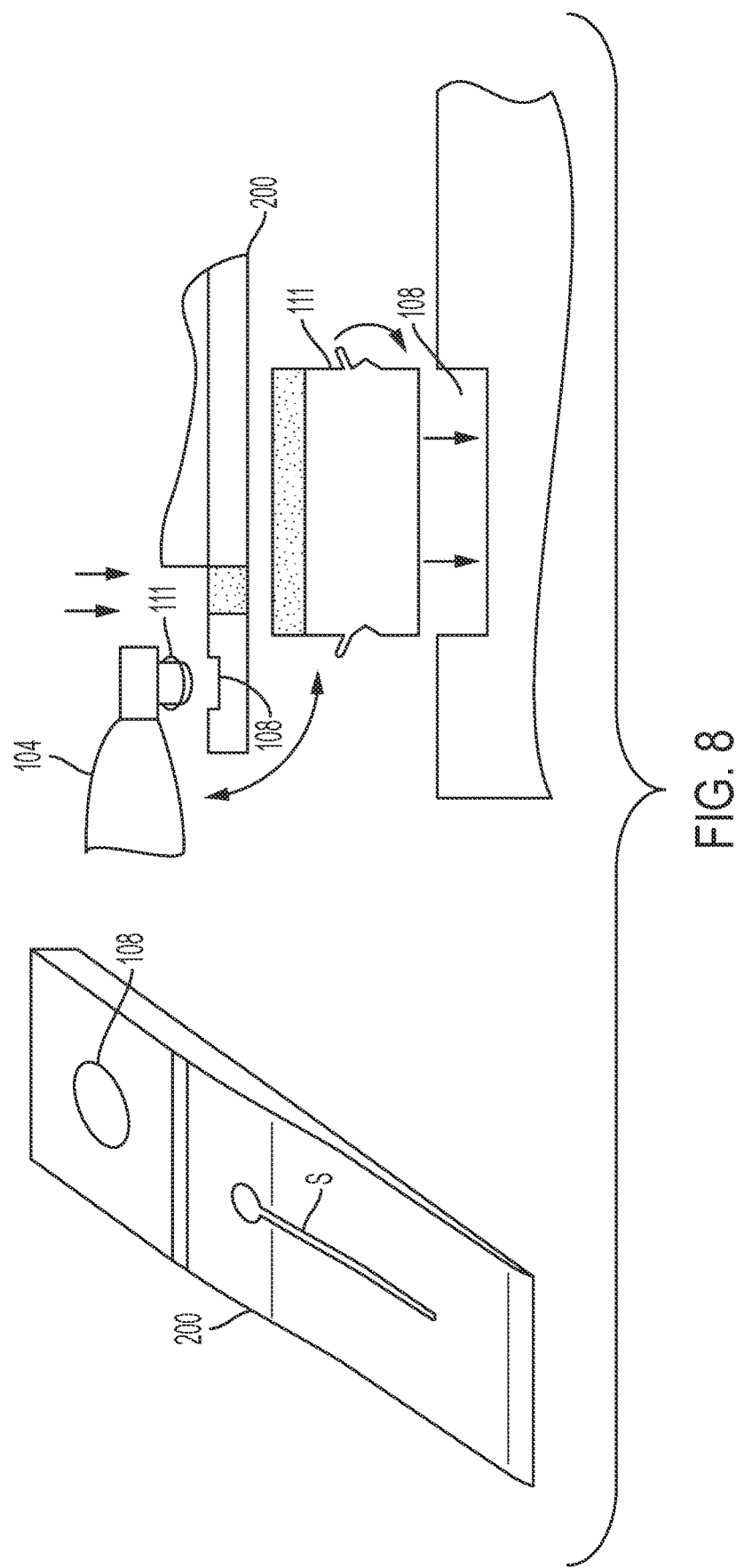
FIG. 8 illustrates a perspective view of a guiding track and an exploded, side view of a fluid bag attachment mechanism, according to at least one aspect of the present disclosure.

The fluid bag 104 comprises a threaded rotating nozzle 111, which secures the fluid bag 104 to the guiding track 200 by way of the threaded attachment mechanism 109. An additional view of the threaded rotating nozzle 111 is illustrated in FIG. 8. As will be discussed in greater detail below, the proper attachment of the fluid bag 104 to the guiding track 200 can initiate an opening motion or a release of a valve 108 defined within the connector port 105. The valve 108 can comprise a press-seal in some instances. In other instances, the valve 108 comprises any suitable rubber gasket which prevents fluid movement or flow before the fluid bag 104 is completely attached to the guiding track 200. That is, the saline solution and/or the medicament remain in the fluid bag 104 until the valve 108 is activated by properly attaching the fluid bag 104 to the guiding track 200. In some instances, the fluid bag 104 comprises a modular system-critical component attachment mechanism 900, as illustrated in FIG. 19. The modular system-critical component attachment mechanism 900 is configured to ensure the proper attachment of the fluid bag 104 to the guiding track 200 before use of the needle guiding system 100.

The first use of a fluid bag 104 with the needle guiding system 100 requires a sterile flush. The compression sleeve 102 can incorporate an external flushing device in some instances. In some embodiments, the fluid bag 104 comprises a single chamber. In other embodiments, the fluid bag 104 comprises multiple chambers. For example, the fluid bag 104 can comprise a separate small chamber containing sterile water used to flush the needle guiding system 100 prior to use, as will be discussed in greater detail below. In other instances, the compression sleeve 102 is equipped with a multi-chamber fluid bag. The multi-chamber fluid bag consists of one large chamber with the intended solution and one significantly smaller chamber adjacent to the connector port 105 containing sterile water. The sterile water is configured to flush anything previously within the needle guiding system 100 and remove any irregularities along the flow path such as air. The irregularities can be expelled from a flush hole, as will be discussed in greater detail below.

Figure 2:
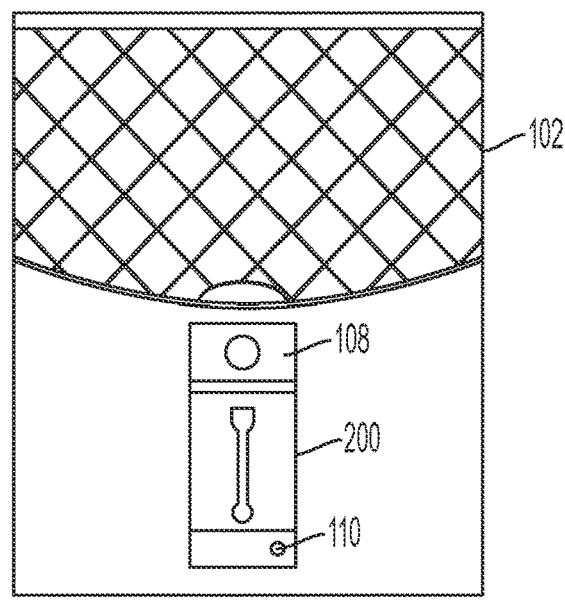
FIG. 2 illustrates a top view of portions of the needle insertion system of FIG. 1, according to at least one aspect of the present disclosure.
Figure 2A:
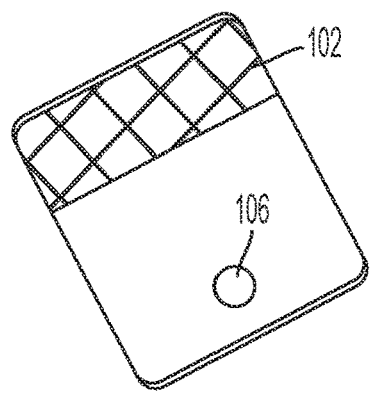
FIGS. 2A and 2B illustrate additional top views of the needle insertion system of FIG. 1 with certain components removed for illustrative purposes, according to at least one aspect of the present disclosure.

Referring to FIG. 2A, the needle guiding system 100 comprises a guiding track 200 for use with various needle block assemblies, such as the needle block assembly 300, which will be discussed in greater detail below. The guiding track 200 is configured to guide a needle block assembly down a predetermined path in order to insert a needle into a vein at a predetermined location. The guiding track 200 can be secured to the compression sleeve 102 by any suitable means. As described above, in many embodiments, the guiding track 200 is attached to the compression sleeve 102. In some instances the guiding track 200 comprises a flush hole for the release of a saline solution from the fluid bag 104 during a flushing procedure prior to use of the needle guiding system 100, as discussed above.

Figure 2B:
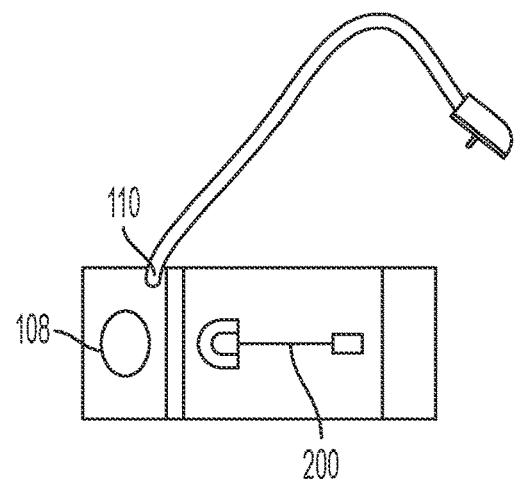

Referring to FIG. 2B, the needle guiding system 100 can include a cost effective option which allows a user to safely and efficiently swap out a used fluid bag for a new fluid bag. In some instances, the guiding track 200 comprises a pre-threaded tubing port 110. For example, the needle guiding system 100 can include pre-threaded tubing that is connected to the needle guiding system 100 on the side of the fluid bag 104 so that the fluid bag can easily be switched or "hot swapped" during a procedure.

Figure 4:
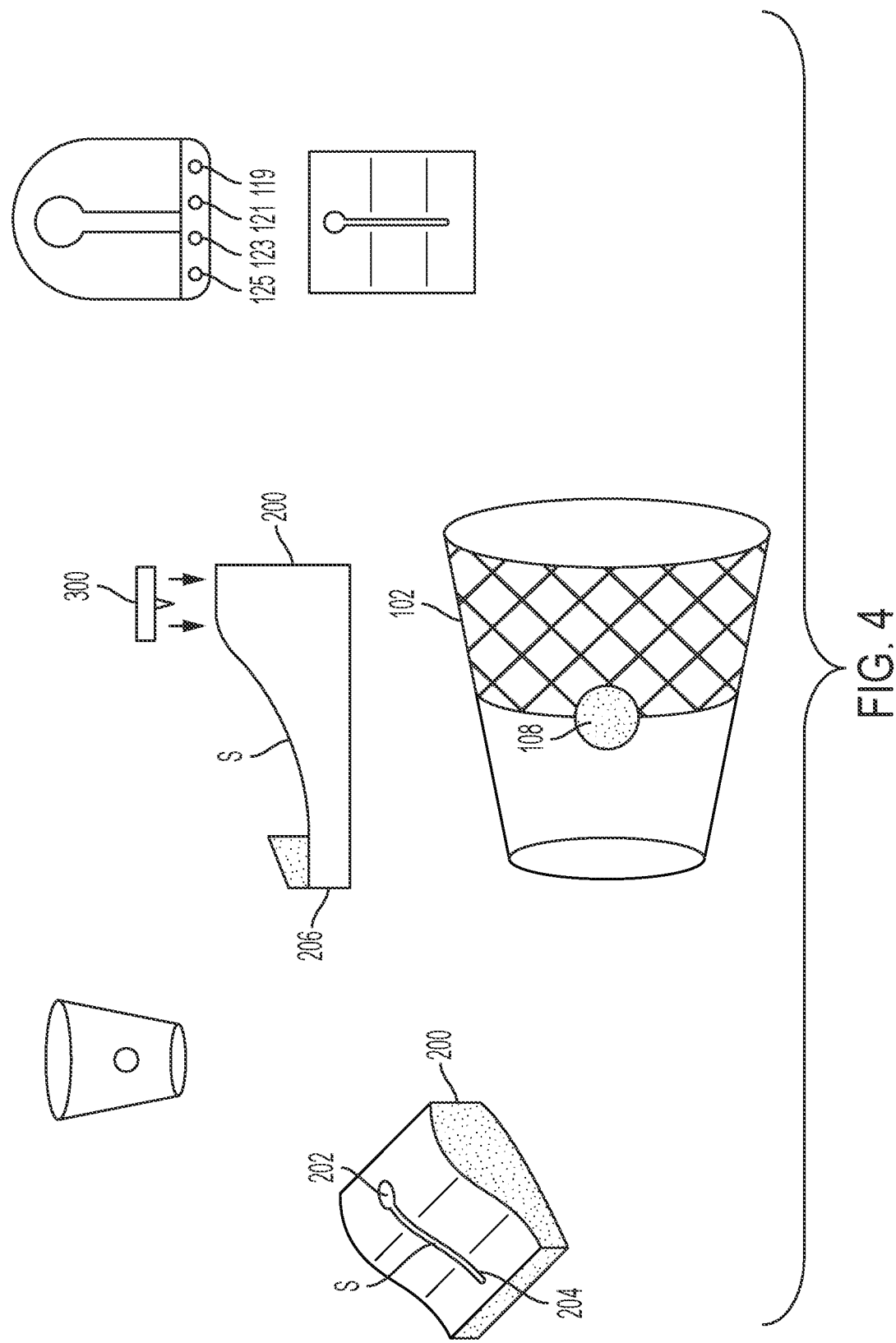
FIG. 4 illustrates various views of the guiding track of FIG. 3, according to at least one aspect of the present disclosure.
Figure 12:
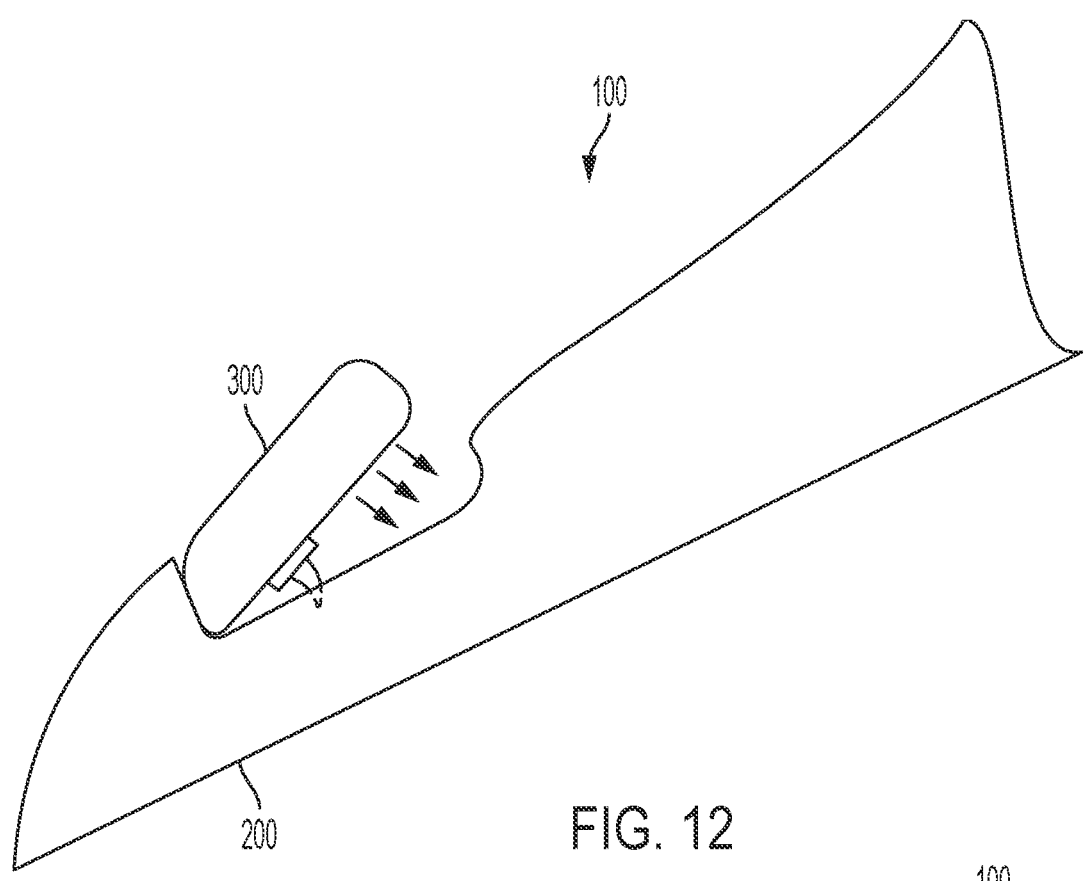
FIG. 12 illustrates a perspective view of the needle block assembly and the guiding track of FIG. 7, according to at least one aspect of the present disclosure.

Referring to FIG. 3, the guiding track 200 can include a user interface 113, which includes the output of a series of fluid flow pressure sensors 208 that are configured to alert a user as to the status of fluid flow during use of the needle guiding system 100. The user interface 113 can include LED indicators to alert a user in certain instances. The user interface 113 can comprise a series of mechanical gauges or LED indicators 119, 121, and 123 as illustrated in FIG. 12, for example. Referring to FIG. 4, the mechanical gauges and/or LED indicators 119, 121, and 123 can pertain to various aspects of the needle guiding system 100. For example, the mechanical gauges and/or LED indicators 119, 121, and 123 can pertain to fluid flow control, pressurized delivery, or system failure, for instance. In many instances, the needle guiding system 100 comprises a fail-safe gauge 125 to prevent catastrophic events. The mechanical gauges and/or LED indicators 119, 121, and 123 are positioned to be visible whether or not the user has inserted the needle block assembly 300 in the guiding track 200. The guiding track 200 can also comprises two pressure sensors. One sensor is positioned between the fluid bag 104 and a pressurized regulator 210. Another sensor is positioned between the pressurized regulator 210 and the catheter entrance of the needle block 300, as will be discussed below. The fluid pressurization regulator 210 serves to regulate fluid flow through the guiding track 200.

Referring to FIGS. 3A and 3B, the guiding track 200 comprises a starting platform 202 and a landing platform 204. In some instances, the guiding track 200 comprises rails 203 defined therein which are configured to receive pegs or tracks on the bottom of the needle block assembly 300, as will be discussed in greater detail below. For example, the needle block 300 can slidably engage the guiding track 200 such that movement of the needle block 300 relative to the guiding track 200 is confined along a single path, i.e., toward the landing platform 204. The guiding track 200 comprises a lock 206 defined in the landing platform 204 of the guiding track 200. The lock 206 comprises a level area configured to receive the needle block assembly 300 in order to secure the needle block assembly 300 during use.

Figure 5D:
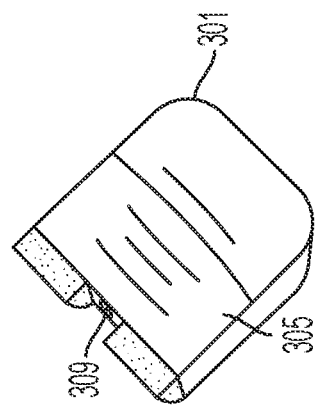
FIGS. 5B-5F illustrates various views of a needle block assembly configured for use with the needle guiding system illustrated in FIGS. 1-4, according to at least one aspect of the present disclosure.
Figure 5C:
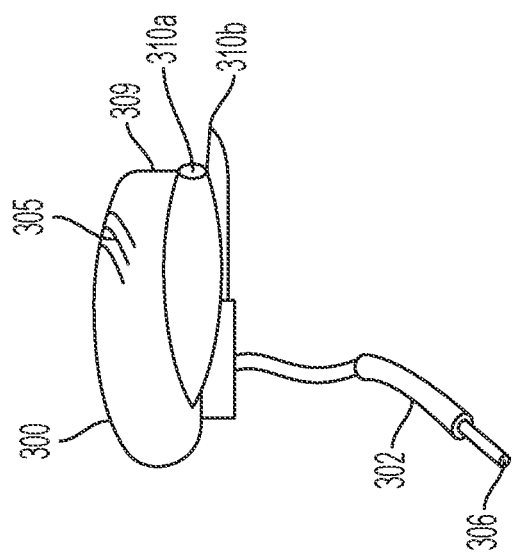
Figure 5B:
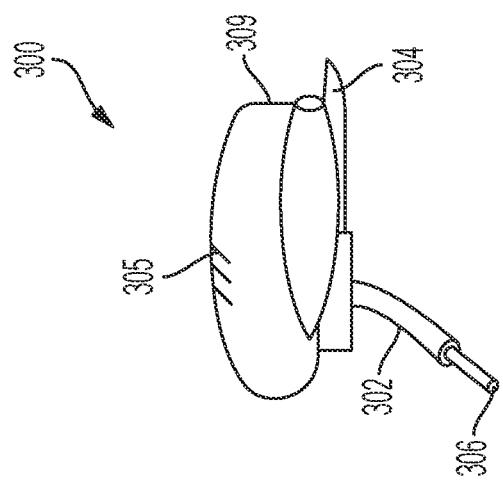
Figure 13:
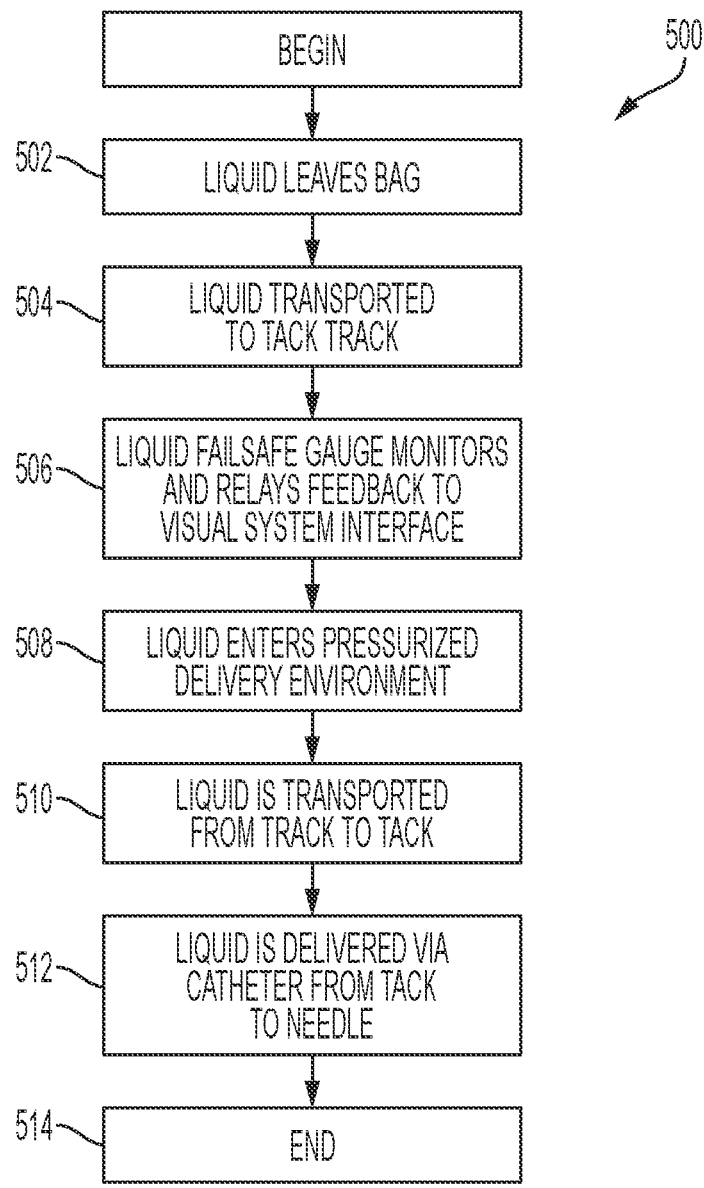
FIG. 13 illustrates a timeline of the fluid flow path of FIG. 12A, according to at least one aspect of the present disclosure.

Referring to FIGS. 5 and 5A, the needle block assembly 300, also referred to as a "tack" or "cart", comprises a body portion 301, which defines an inner cavity that enables fluid from the fluid bag 104 to flow through the guiding track 200 and into the needle block assembly 300. The body portion 301 of the needle block assembly 300 also comprises a thumb grip portion 305 on the outer surface. The body portion 301 comprises a curvature defining pegs 310a and 310b (FIG. 5C), which provide guidance as the needle block assembly 300 travels along the rails 304 of the guiding track 200. An example of the curvature of the body portion 301 is illustrated in FIG. 13.

Referring again to FIGS. 5 and 5A, the needle block assembly 300 comprises a latch 304 configured to lock the needle block assembly 300 into the lock 206 in the landing platform 204. In various embodiments, the latch 304 comprises a tailhook configured to engage the lock 206 defined in the landing platform 204. In some embodiments, the needle block assembly 300 comprises a single tailhook latch 304, although embodiments are envisioned wherein more than one tailhook latch 304 is used to secure the needle block assembly 300 to the guiding track 200. For example, the needle block assembly 300 in its normal state has a slightly-slanted tailhook latch 304, which snaps into the guiding track 200 resulting in an audible 'click'. In other instances, the tailhook can provide tactile feedback when the needle block assembly 300 is fully seated in ending or landing zone of the guiding track 200.

Figure 7A:
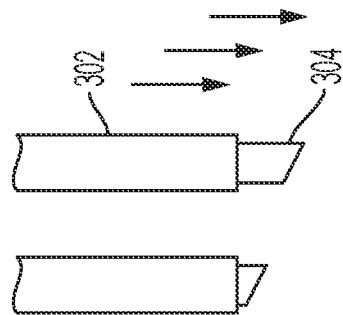
FIG. 7A illustrates views of a needle and catheter, according to at least one aspect of the present disclosure.

The needle block assembly 300 comprises a needle assembly 302 extending from the bottom of the body portion 301. The needle assembly 302 comprises an integral needle and catheter 306 extending within the needle. An end of the catheter 306 can extend beyond the edge of the needle in certain instances when the needle assembly 302 is fully seated in the landing zone of the guiding track 200. Referring to FIG. 7A, the catheter 304 is positioned within the needle assembly 302 as the needle block assembly 300 travels through the guiding track 200 along a slope thereof from the starting platform to the landing platform, for example. See also FIG. 4. The catheter 306 remains within the needle 302 until the needle block 300 is snapped into place by the tailhook latch 304 engaging the lock 206 as the needle block assembly 300 reaches the landing platform 204. Once the tailhook latch 304 is secure, the user can insert the needle 302 into the vein at the predetermined insertion point. Once the user inserts the needle 302 into the vein, the user can advance the catheter 306 from the needle 302 in order to deliver fluids into the vein. The catheter 304 can comprise a transitory catheter in some embodiments. A transitory catheter is a mechanism that may be included in certain needle block assemblies to provide alternate methodology. As the tailhook latch 304 snaps into place, the catheter 304, which is threaded through the soft-edged needle 302, is pushed further into the vein insertion point. This arrangement can eliminate the need for a sharp-edged needle and can provide a protective arrangement for avoiding unintentional user harm.

Figure 5E:
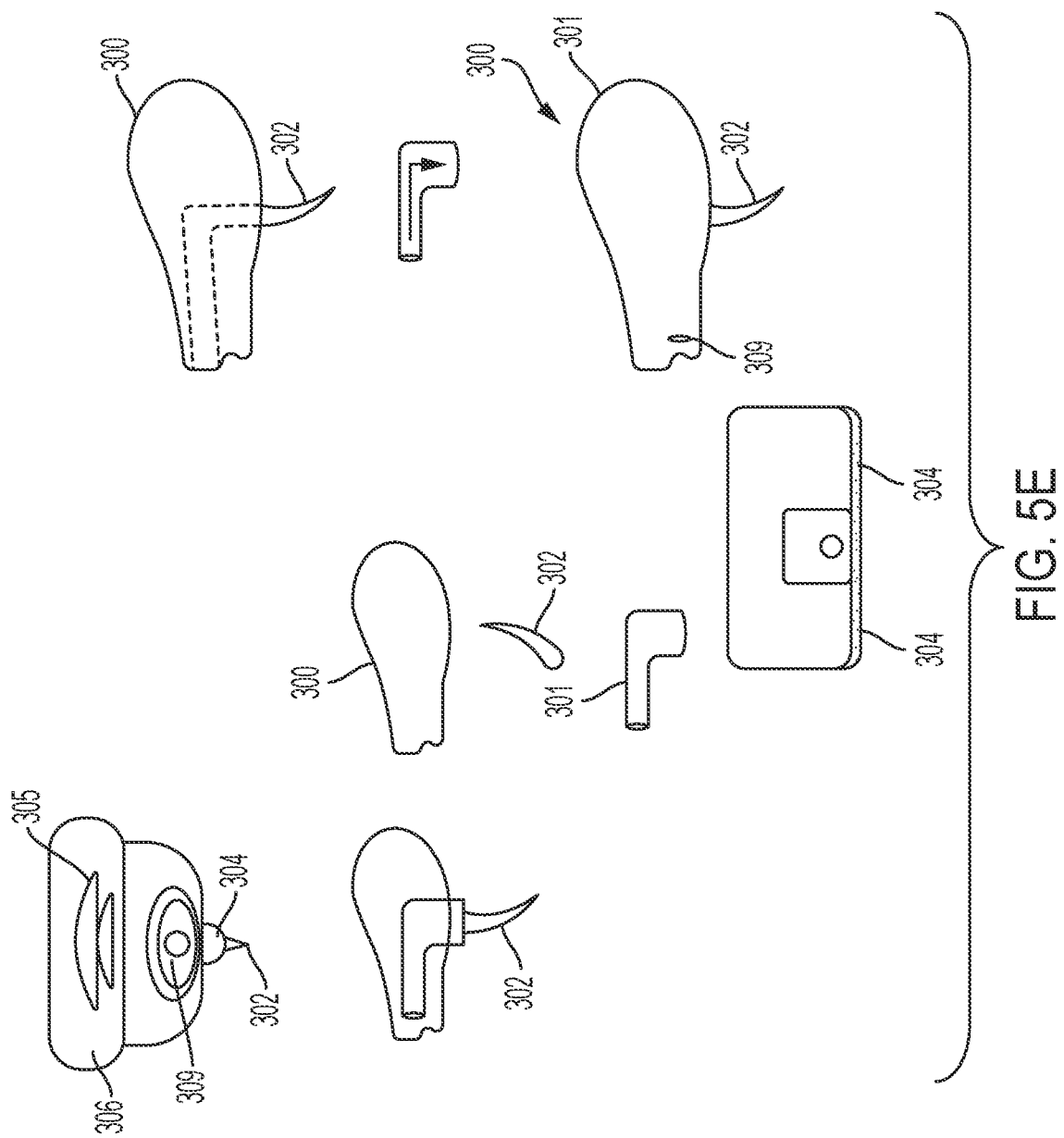
Figure 9:
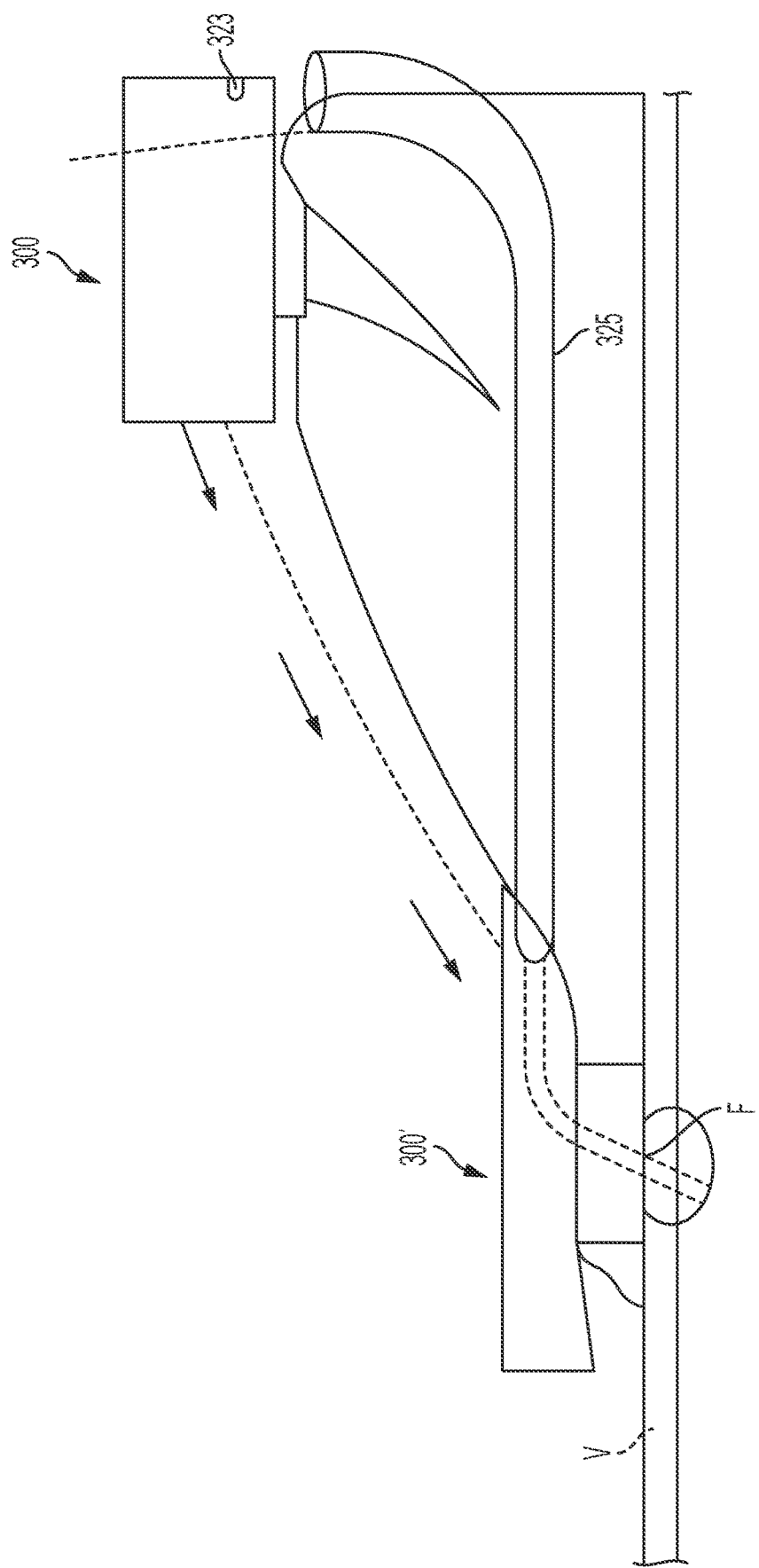
FIG. 9 illustrates another exploded, side view of a fluid bag attachment mechanism of along with additional portions of a needle insertion assembly, according to at least one aspect of the present disclosure.
Figure 11:
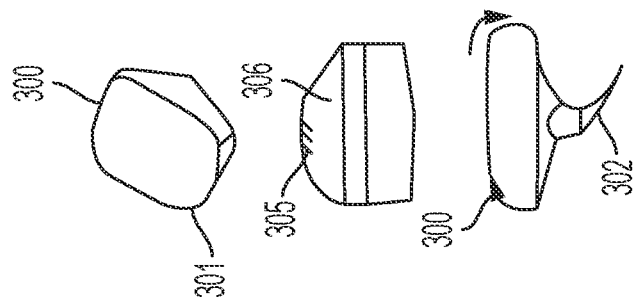
FIG. 11 illustrates views of different aspects of the needle block assembly of FIG. 5, according to at least one aspect of the present disclosure.

FIG. 9 illustrates the needle guiding system of FIG. 1 with additional components. As illustrated in FIG. 9, the needle block assembly 300 comprises a port 323 for fluid to flow into the needle block assembly 300 once the needle block assembly 300 is seated in a final, locked position 300'. For example, the port 323 aligns with the fluid tube 325 when the needle block assembly 300' is seated in the locked position. Referring now to FIG. 5E, the needle block assembly 300 can comprise a gasket port 309 configured to operably seal a fluid path, which runs from the fluid bag 104 through the guiding track 200, through the port 323 and the needle block assembly 300 to ultimately reach the needle 302 to be inserted in the vein V (see also FIG. 9). The gasket port 309 can comprise rubber or any other suitable material. Embodiments are contemplated wherein an open channel runs through the guiding track 200 and the needle block assembly 300, although any other suitable channels which enable fluid to flow from the fluid bag 104 to the needle assembly 302 are suitable for use with the needle guiding system 100 described herein.

Figure 6:
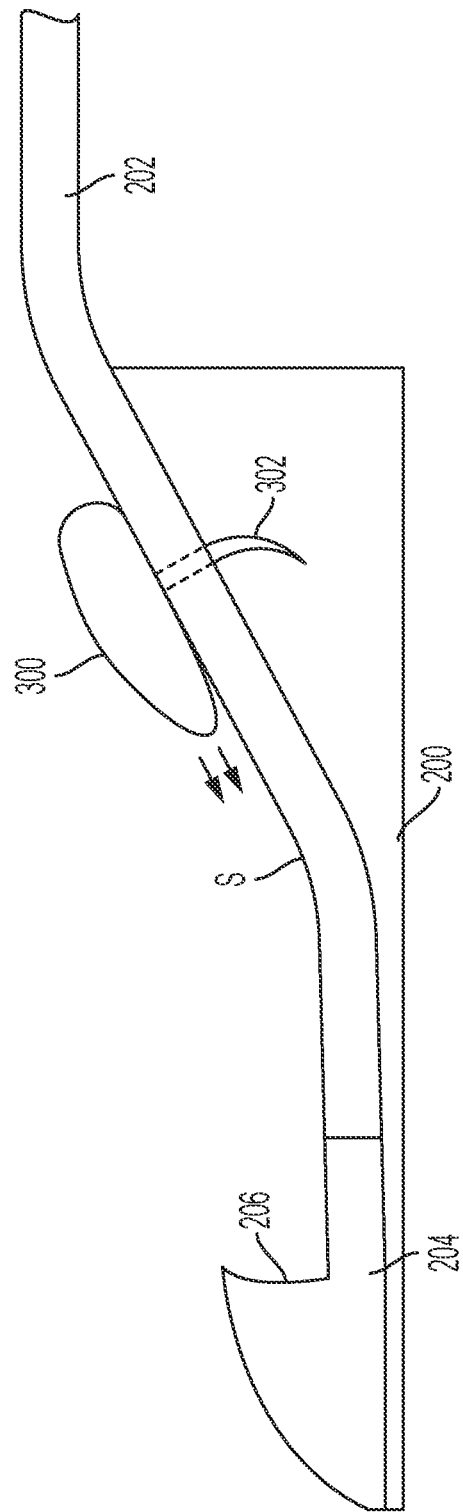
FIG. 6 illustrates a side view of the needle guiding system of FIG. 1 during a needle insertion operation, according to at least one aspect of the present disclosure.
Figure 6A:
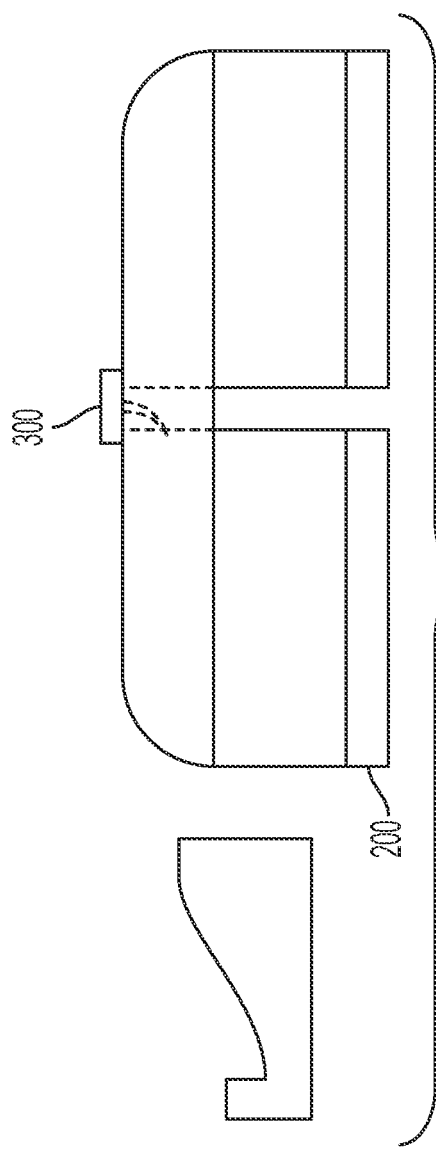
FIG. 6A illustrates additional views of the guiding track, according to at least one aspect of the present disclosure.

Referring now to FIGS. 6 and 6A, the needle guiding system 100 is depicted during use. As seen in FIG. 6, at the beginning of a procedure, a user positions the needle block assembly 300 at the starting platform 202 of the guiding track 200. As discussed above, the guiding track 200 comprises rails 304 defined therein which guide the needle block assembly 300 along a predetermined path from the starting platform 202 to the landing platform 204. As the needle block 300 assembly reaches the landing platform 204, the tailhook latch 304 of the needle block assembly 300 is configured to engage the lock 206 defined within the landing platform 204 of the guiding track 200 as discussed above.

The guiding track 200 and the needle block assembly 300 of the needle guiding system 100 can provide a unique benefit. For example, the rails 304 of the guiding track 200 can include a narrow-guided way for the pegs 310a and 310b on the underside of the needle block assembly 300. The narrow-guided way streamlines the placement process of the needle block assembly 300 and reduces the chance of missing the intended needle insertion target. The guiding track 200 includes an s-curved slope S between the starting platform 202 and the landing platform 204. The flat starting platform 202 is configured for the user to align the needle block assembly 300 in the guiding track 200 before initiating any sliding motions. The s-curve slope S is configured to ease the topographic drop from the starting platform 202 to a vein puncture point P positioned below the landing platform 204.

Figure 7:
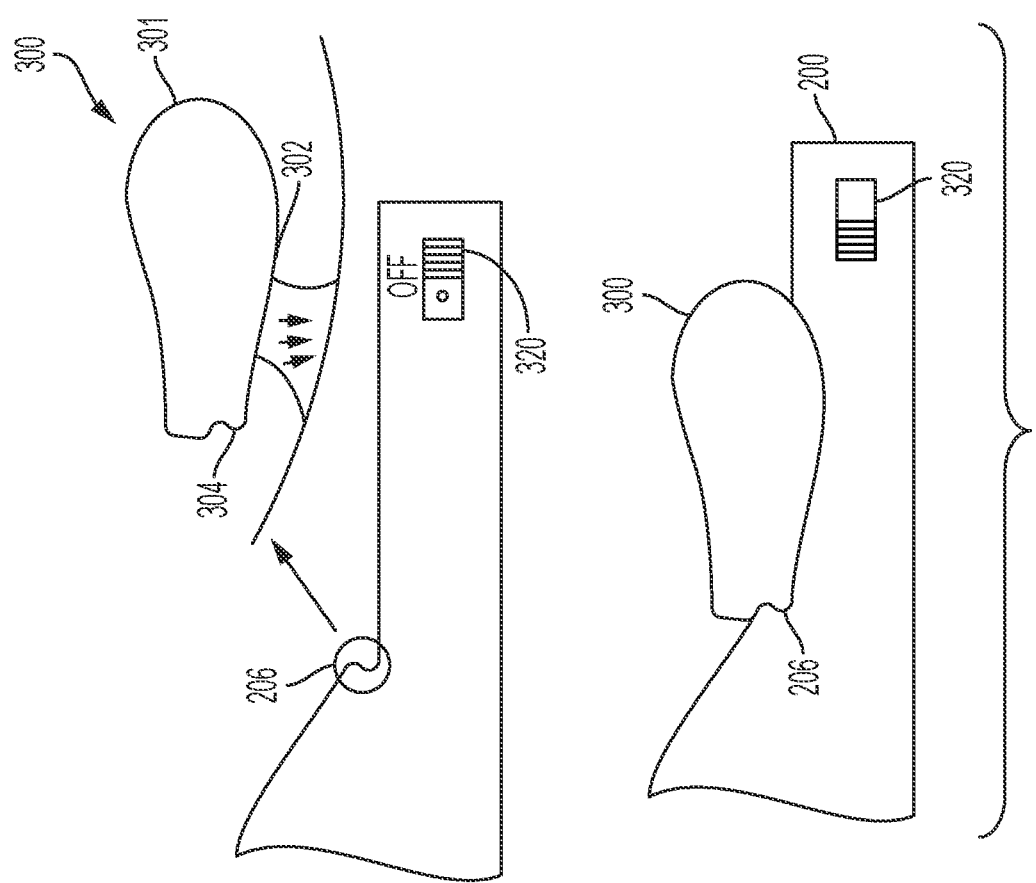
FIG. 7 illustrates side views of the needle block assembly and the guiding track, according to at least one aspect of the present disclosure.

Turning to FIG. 7, needle block release mechanisms are illustrated. The needle guiding system 100 can comprise a variety of suitable release mechanisms, which allow a user to remove the needle block assembly 300 in order to remove the needle 302 from a patient's vein. For example, the needle guiding system 100 comprises a release mechanism 320, which pops the tailhook latch 304 out of the lock 206. Once the tailhook latch 304 is removed from the lock 206, a user is free to retract the needle block assembly 300 along the guiding track 200 and remove the needle block assembly 300. The release mechanism 320 can comprise a press button in some instances. In other instances, the release mechanism 320 can comprise a lever or release latch, although any suitable release mechanism can be used to release the needle block assembly 300 from the guiding track 200.

Figure 10:
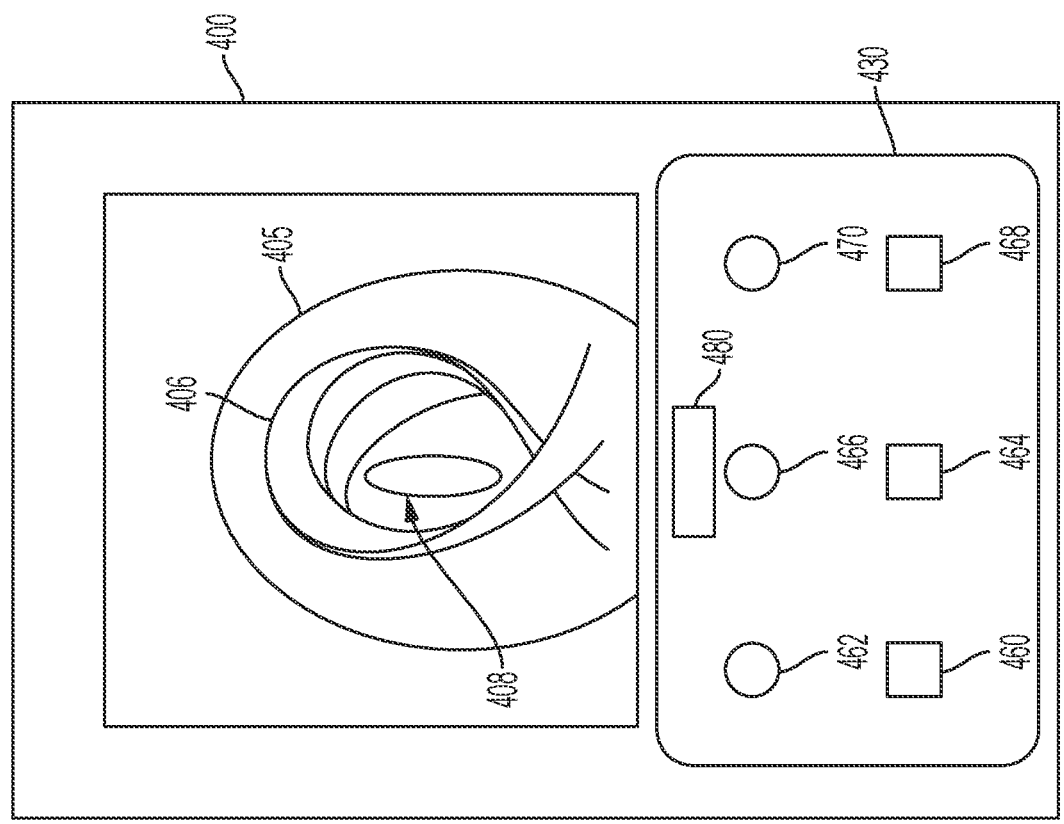
FIG. 10 illustrates various system interfaces, according to at least one aspect of the present disclosure.

FIG. 10 illustrates various system indicators, which are components of a user interface 430, which is described in greater detail below. The user interface 430 is compatible with various needle guiding systems described herein. For example, a needle block assembly 400 can include a user interface 430, which includes a series of fluid flow pressure sensors that are configured to alert a user as to the status of fluid flow during use of the needle guiding system 100. The system interface 430 comprises a series of mechanical gauges and/or indicators in many instances. The user interface 430 can include LED indicators to alert a user in certain instances. The user interface 430 can comprise a series of mechanical gauges 460, 464, and 468 as illustrated in FIG. 10, for example. Referring to FIG. 10, the mechanical gauges 460, 464, and 468 can pertain to various aspects of the needle guiding system 100. For example, the mechanical gauges 460, 464, and 468 can pertain to fluid flow control, pressurized delivery, or system failure, for instance. The user interface 430 also comprises a series of LED indicators 462, 466, and 470, each of which correspond to the mechanical gauges for fluid flow control, pressurized delivery, or system failure, for instance. In many instances, the needle guiding system 100 comprises a fail-safe gauge 480 to prevent catastrophic events. The LED indicators 462, 466, and 470 are positioned to be visible whether or not the user has inserted the needle block assembly 400 in a guiding track 420.

Figure 12A:
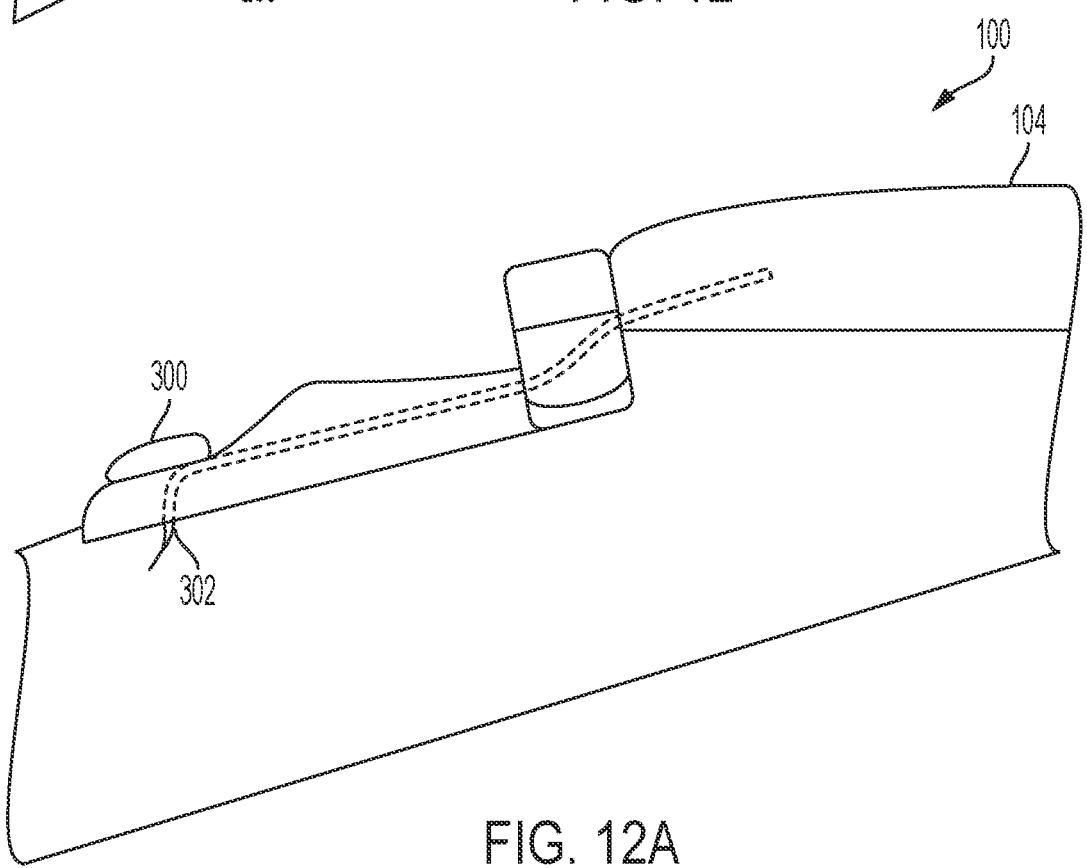
FIG. 12A illustrates a side view of the needle guiding system with the fluid flow path of FIG. 6 defined therein, according to at least one aspect of the present disclosure.

FIGS. 12 and 12A illustrate an exemplary embodiment of the fluid flow path F while the needle guiding system 100 is in use. At the beginning of a procedure, the fluid bag 104 is secured to the guiding track 200 on the compression sleeve 102 as indicated above. Once the fluid bag is secured to the guiding track 200, a user can position the needle block assembly 300 at the starting point 202 of the guiding track 200. The user moves the needle block assembly 300 along the guiding track 200 until the needle block assembly 300 reaches the ending point or landing platform 204 of the guiding track 200. Once the needle block assemble 300 reaches the landing platform 204, the tailhook latch 304 of the needle block assembly 300 clicks into place within the lock 206. Once the tailhook latch 304 clicks into place, fluid is free to flow from the fluid bag 104, through the guiding track 200 until it reaches the needle block assembly 300. The fluid flows from the needle block assembly 300 into the catheter 306 to be administered into the vein. For example, when the needle block assembly 300 is fully seated in the landing zone of the guiding track 200, a fluid pathway of the needle can move into alignment with a fluid tube or conduit of the guiding track 200 such that fluid can flow from the fluid bag 104 through the fluid conduit in the track 200, through the needle assembly 302, and into a patient's bloodstream. A fluid pathway to the needle assembly 302 can include an opening in the needle block assembly 300 that moves into alignment with the fluid pathway in the track 200 only when the needle block assembly 300 is fully seated in the landing zone and locked into place.

FIG. 13 illustrates an exemplary fluid flow timeline 500 in detail. At step 502, the fluid leaves the fluid bag 104. As discussed above in greater detail, the fluid can comprise a saline solution and/or a medicament. At step 504, the fluid flows to the guiding track 200. As the fluid flows through the guiding track 200, the fluid fail-safe gauge 125 monitors the fluid flow and transmits feedback to the user interface in step 506, as discussed above. While traveling through the guiding track 200, the fluid enters a pressurized delivery environment in step 508, as will be discussed in greater detail below. In step 510, the fluid flows from the guiding track 200 to the needle block assembly 300. Once the fluid reaches the needle block assembly 300, the liquid reaches the vein by way of the catheter 306 within the needle 302.

Figure 14:
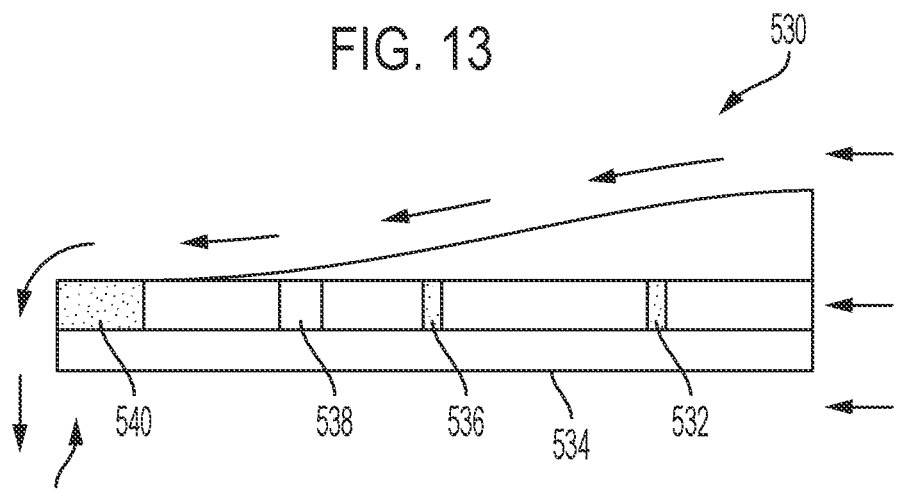
FIG. 14 illustrates a pressure regulation system, according to at least one aspect of the present disclosure.

FIG. 14 illustrates a pressurized delivery environment 530 within the guiding track 200. The pressurized delivery environment 530 comprises a pressure monitor 532 configured to measure fluid pressure within the guiding track 200. The pressurized delivery environment 530 also comprises a pressure regulator 534 configured to modify the pressure within the guiding track 200 based on the fluid pressure measurement determined by the pressure monitor 532. The pressurized delivery environment 530 further comprises a pressure monitor 536 configured to measure fluid pressure within the guiding track 200 at a point distal to the pressure monitor 532 and pressure regulator 534. The pressurized delivery environment 530 also comprises a system interface sensor 538, which is configured to transmit feedback regarding fluid pressure within the guiding track 200 to the user interface 113 of the guiding track 200.

Figure 5F:
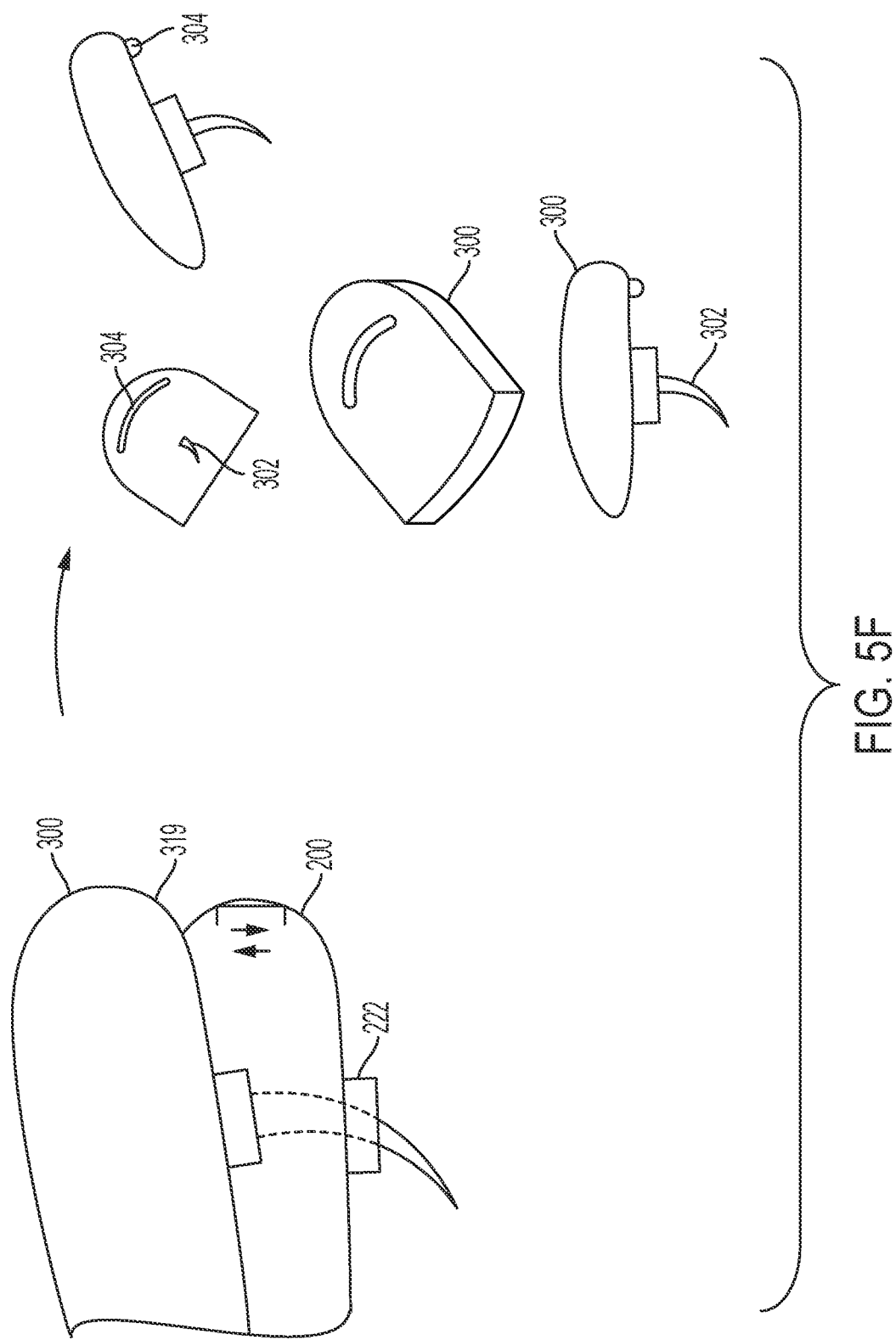

FIGS. 15 and 15A illustrate an exemplary embodiment of a sensor system 600 in accordance with various embodiments of the needle delivery systems disclosed herein. The sensor system 600 comprises a fluid bag sensor 601. The fluid bag sensor 601 is configured to monitor fluid levels within the fluid bag 104. The fluid bag sensor 601 can also be configured to monitor whether the fluid bag 104 is attached to the guiding track 200. The sensor system 600 also comprises a pressure sensor 602 configured to monitor pressure within the guiding track 200. The sensor system 600 also comprises a pressure processing unit 604, which is configured to regulate the pressure within the guiding track 200. The sensor system 600 also comprises a second pressure sensor 606, which is positioned distally with respect to the pressure sensor 602 and the pressure processing unit 604. The second pressure sensor 606 is also configured to monitor pressure within the guiding track 200. The sensor system 600 also comprises a needle block assembly or tack sensor 608 configured to monitor various aspects of the needle block assembly 300. For example, the needle block assembly sensor 608 is configured to monitor a position of the needle block assembly 300. In some instances, the needle block assembly sensor 608 is configured to monitor a status of the needle block assembly 300. Referring to FIG. 5F, in some instances the needle guiding system does not comprise a needle block assembly. For example, the needle block assembly can comprise a solid external lip 319 which controls fluid passage from the fluid bag 104 and whether fluid can flow from the fluid bag 104 into the guiding track 200. The solid external lip 319 is configured to work in conjunction with pressure regulators, such as the pressure regulator 414. The solid external lip 319 is also configured to control flush systems of the needle guiding system. For example, a sterile flush unit 612 is also illustrated in FIG. 15A. The sterile flush unit 612 is configured for use during a sterile flush procedure as described above.

Figure 16:
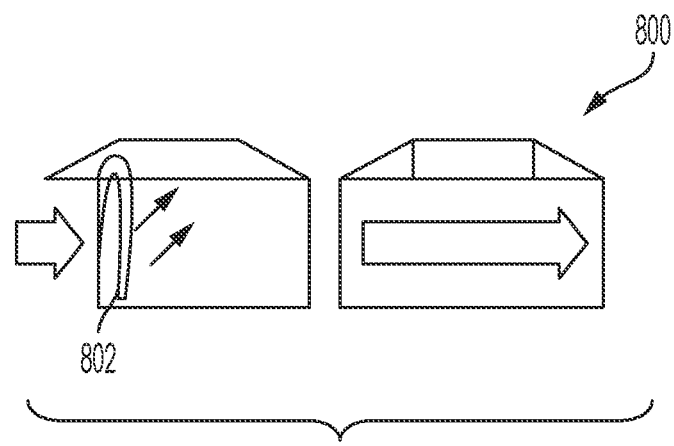
FIG. 16 illustrates a valve system compatible with various needle guiding systems, according to at least one aspect of the present disclosure.
Figure 17:
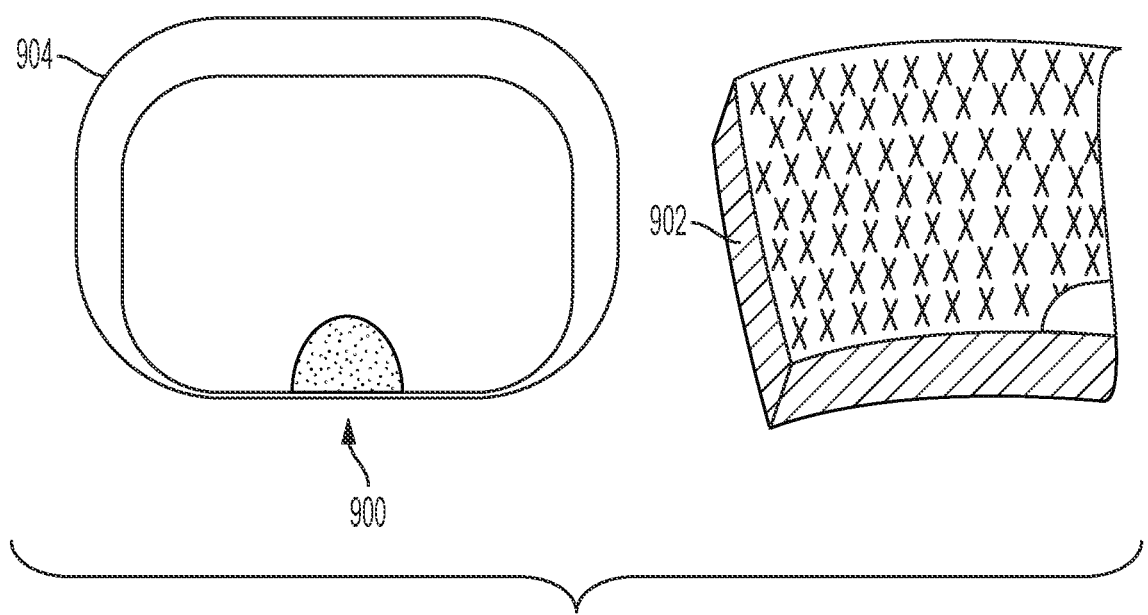
FIG. 17 illustrates an attachment mechanism for a fluid bag compatible with various needle guiding systems, according to at least one aspect of the present disclosure.

FIG. 16 illustrates a valve system 800 which is compatible with various needle guiding systems described herein. A valve 802 is configured to prevent fluid flow from the fluid bag 104 until the fluid bag 104 is properly attached to the guiding track 200. A valve 802 can also be positioned within the needle block assembly 300 in some instances in order to prevent fluid flow from the needle block assembly 300 before the needle 302 is properly inserted into the vein and before the catheter 306 is advanced from the needle 304. For example, a valve can be positioned at the exit of the guiding track 200. A pressurization on-off gauge can operably control one of or more of the valves of the valve system 800. In some instances, the valve 802 is configured to compliment various pressure monitoring sensors described above. In some instances, a status of the valve 802 can be depicted on the user interface 113 of the guiding track 200.

Figure 18:
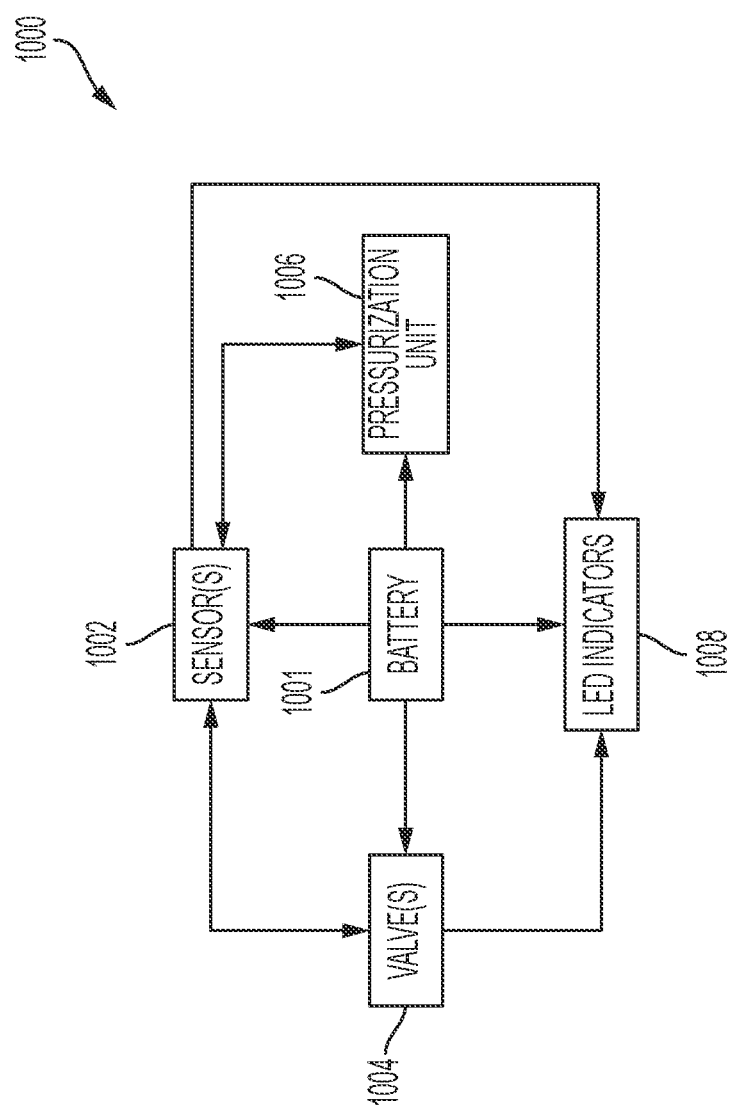
FIG. 18 illustrates a control system for regulating fluid flow comprising various components of the needle guiding system of FIG. 1, according to at least one aspect of the present disclosure.

FIG. 18 illustrates a basic schematic for a control system 1000 configured for use with various needle guiding systems described herein. A battery 1001 is configured to provide power to the sensors 1002, the valve(s) 1004, the pressurization unit 1006, and the analog system gauges or the LED indicators 1008. The sensors 1002 are configured to monitor at least one status of needle guiding systems described herein. The sensors 1002 can monitor a status of the valve(s) 1004 or a status of the pressurization unit 1006. The sensors 1002 can also be configured to monitor the position of a needle block assembly. For example, the sensors 1002 can determine whether a needle block assembly has been properly seated in the landing platform of the guiding track. The LED indicators 1008 are configured to alert a user of various aspects of the needle guiding systems described herein. The LED indicators 1008 are similar to the LED indicators described above in relation to FIG. 3. In various instances, a control circuit for implementing the control system 1000 can be embodied or encapsulated within the guiding track 200 or in the compression sleeve 102, for example.

In use, a person can quickly and easily install the IV needle assemblies disclosed herein. Because the needle is guided into place at a predefined angle and position, persons without formal training may be able to use the needle guiding systems disclosed herein in certain circumstances. For example, where access to doctors, nurses, or trained medical personnel is limited or scarce, such as for certain military and/or humanitarian efforts, the needle assemblies herein can be utilized to delivery medication and/or other fluids to patients. For example, a person can simply pick of the needle block assembly and align it with the starting line of the guiding track. The needle block assembly can then be moved down the guiding track to the finish line, where a sufficient force is configured to seat the needle block assembly. For example, the needle block assembly can "click" into place. When fully seated, a final gasket in the needle block assembly can open. Additionally, the catheter of the needle assembly can be pushed down through the needle to protect the tip of the needle while the needle remains positioned in the patient's vein.

In various instances, when the needle is positioned in the patient's vein, a "hot-swap" can be initiated, in which a fluid bag is replaced with another fluid bag simply by unscrewing the nozzle and threadably attaching another fluid bag.

While several forms have been illustrated and described, it is not the intention of Applicant to restrict or limit the scope of the appended claims to such detail. Numerous modifications, variations, changes, substitutions, combinations, and equivalents to those forms may be implemented and will occur to those skilled in the art without departing from the scope of the present disclosure. Moreover, the structure of each element associated with the described forms can be alternatively described as a means for providing the function performed by the element. Also, where materials are disclosed for certain components, other materials may be used. It is therefore to be understood that the foregoing description and the appended claims are intended to cover all such modifications, combinations, and variations as falling within the scope of the disclosed forms. The appended claims are intended to cover all such modifications, variations, changes, substitutions, modifications, and equivalents.

The foregoing detailed description has set forth various forms of the devices and/or processes via the use of block diagrams, flowcharts, and/or examples. Insofar as such block diagrams, flowcharts, and/or examples contain one or more functions and/or operations, it will be understood by those within the art that each function and/or operation within such block diagrams, flowcharts, and/or examples can be implemented, individually and/or collectively, by a wide range of hardware, software, firmware, or virtually any combination thereof. Those skilled in the art will recognize that some aspects of the forms disclosed herein, in whole or in part, can be equivalently implemented in integrated circuits, as one or more computer programs running on one or more computers (e.g., as one or more programs running on one or more computer systems), as one or more programs running on one or more processors (e.g., as one or more programs running on one or more microprocessors), as firmware, or as virtually any combination thereof, and that designing the circuitry and/or writing the code for the software and or firmware would be well within the skill of one of skill in the art in light of this disclosure. In addition, those skilled in the art will appreciate that the mechanisms of the subject matter described herein are capable of being distributed as one or more program products in a variety of forms, and that an illustrative form of the subject matter described herein applies regardless of the particular type of signal bearing medium used to actually carry out the distribution.

Instructions used to program logic to perform various disclosed aspects can be stored within a memory in the system, such as dynamic random access memory (DRAM), cache, flash memory, or other storage. Furthermore, the instructions can be distributed via a network or by way of other computer readable media. Thus a machine-readable medium may include any mechanism for storing or transmitting information in a form readable by a machine (e.g., a computer), but is not limited to, floppy diskettes, optical disks, compact disc, read-only memory (CD-ROMs), and magneto-optical disks, read-only memory (ROMs), random access memory (RAM), erasable programmable read-only memory (EPROM), electrically erasable programmable read-only memory (EEPROM), magnetic or optical cards, flash memory, or a tangible, machine-readable storage used in the transmission of information over the Internet via electrical, optical, acoustical or other forms of propagated signals (e.g., carrier waves, infrared signals, digital signals, etc.). Accordingly, the non-transitory computer-readable medium includes any type of tangible machine-readable medium suitable for storing or transmitting electronic instructions or information in a form readable by a machine (e.g., a computer).

As used in any aspect herein, the term "control circuit" may refer to, for example, hardwired circuitry, programmable circuitry (e.g., a computer processor including one or more individual instruction processing cores, processing unit, processor, microcontroller, microcontroller unit, controller, digital signal processor (DSP), programmable logic device (PLD), programmable logic array (PLA), or field programmable gate array (FPGA)), state machine circuitry, firmware that stores instructions executed by programmable circuitry, and any combination thereof. The control circuit may, collectively or individually, be embodied as circuitry that forms part of a larger system, for example, an integrated circuit (IC), an application-specific integrated circuit (ASIC), a system on-chip (SoC), desktop computers, laptop computers, tablet computers, servers, smart phones, etc. Accordingly, as used herein "control circuit" includes, but is not limited to, electrical circuitry having at least one discrete electrical circuit, electrical circuitry having at least one integrated circuit, electrical circuitry having at least one application specific integrated circuit, electrical circuitry forming a general purpose computing device configured by a computer program (e.g., a general purpose computer configured by a computer program which at least partially carries out processes and/or devices described herein, or a microprocessor configured by a computer program which at least partially carries out processes and/or devices described herein), electrical circuitry forming a memory device (e.g., forms of random access memory), and/or electrical circuitry forming a communications device (e.g., a modem, communications switch, or optical-electrical equipment). Those having skill in the art will recognize that the subject matter described herein may be implemented in an analog or digital fashion or some combination thereof.

As used in any aspect herein, the term "logic" may refer to an app, software, firmware and/or circuitry configured to perform any of the aforementioned operations. Software may be embodied as a software package, code, instructions, instruction sets and/or data recorded on non-transitory computer readable storage medium. Firmware may be embodied as code, instructions or instruction sets and/or data that are hard-coded (e.g., nonvolatile) in memory devices.

As used in any aspect herein, the terms "component," "system," "module" and the like can refer to a computer-related entity, either hardware, a combination of hardware and software, software, or software in execution.

As used in any aspect herein, an "algorithm" refers to a self-consistent sequence of steps leading to a desired result, where a "step" refers to a manipulation of physical quantities and/or logic states which may, though need not necessarily, take the form of electrical or magnetic signals capable of being stored, transferred, combined, compared, and otherwise manipulated. It is common usage to refer to these signals as bits, values, elements, symbols, characters, terms, numbers, or the like. These and similar terms may be associated with the appropriate physical quantities and are merely convenient labels applied to these quantities and/or states.

Unless specifically stated otherwise as apparent from the foregoing disclosure, it is appreciated that, throughout the foregoing disclosure, discussions using terms such as "processing," "computing," "calculating," "determining," "displaying," or the like, refer to the action and processes of a computer system, or similar electronic computing device, that manipulates and transforms data represented as physical (electronic) quantities within the computer system's registers and memories into other data similarly represented as physical quantities within the computer system memories or registers or other such information storage, transmission or display devices.

One or more components may be referred to herein as "configured to," "configurable to," "operable/operative to," "adapted/adaptable," "able to," "conformable/conformed to," etc. Those skilled in the art will recognize that "configured to" can generally encompass active-state components and/or inactive-state components and/or standby-state components, unless context requires otherwise.

It will be further appreciated that, for convenience and clarity, spatial terms such as "vertical", "horizontal", "up", and "down" may be used herein with respect to the drawings. However, surgical instruments are used in many orientations and positions, and these terms are not intended to be limiting and/or absolute.

Those skilled in the art will recognize that, in general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.). It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to claims containing only one such recitation, even when the same claim includes the introductory phrases "one or more" or "at least one" and indefinite articles such as "a" or "an" (e.g., "a" and/or "an" should typically be interpreted to mean "at least one" or "one or more"); the same holds true for the use of definite articles used to introduce claim recitations.

In addition, even if a specific number of an introduced claim recitation is explicitly recited, those skilled in the art will recognize that such recitation should typically be interpreted to mean at least the recited number (e.g., the bare recitation of "two recitations," without other modifiers, typically means at least two recitations, or two or more recitations). Furthermore, in those instances where a convention analogous to "at least one of A, B, and C, etc." is used, in general such a construction is intended in the sense one having skill in the art would understand the convention (e.g., "a system having at least one of A, B, and C" would include but not be limited to systems that have A alone, B alone, C alone, A and B together, A and C together, B and C together, and/or A, B, and C together, etc.). In those instances where a convention analogous to "at least one of A, B, or C, etc." is used, in general such a construction is intended in the sense one having skill in the art would understand the convention (e.g., "a system having at least one of A, B, or C" would include but not be limited to systems that have A alone, B alone, C alone, A and B together, A and C together, B and C together, and/or A, B, and C together, etc.). It will be further understood by those within the art that typically a disjunctive word and/or phrase presenting two or more alternative terms, whether in the description, claims, or drawings, should be understood to contemplate the possibilities of including one of the terms, either of the terms, or both terms unless context dictates otherwise. For example, the phrase "A or B" will be typically understood to include the possibilities of "A" or "B" or "A and B."

With respect to the appended claims, those skilled in the art will appreciate that recited operations therein may generally be performed in any order. Also, although various operational flow diagrams are presented in a sequence(s), it should be understood that the various operations may be performed in other orders than those which are illustrated, or may be performed concurrently. Examples of such alternate orderings may include overlapping, interleaved, interrupted, reordered, incremental, preparatory, supplemental, simultaneous, reverse, or other variant orderings, unless context dictates otherwise. Furthermore, terms like "responsive to," "related to," or other past-tense adjectives are generally not intended to exclude such variants, unless context dictates otherwise.

It is worthy to note that any reference to "one aspect," "an aspect," "an exemplification," "one exemplification," and the like means that a particular feature, structure, or characteristic described in connection with the aspect is included in at least one aspect. Thus, appearances of the phrases "in one aspect," "in an aspect," "in an exemplification," and "in one exemplification" in various places throughout the specification are not necessarily all referring to the same aspect. Furthermore, the particular features, structures or characteristics may be combined in any suitable manner in one or more aspects.

Any patent application, patent, non-patent publication, or other disclosure material referred to in this specification and/or listed in any Application Data Sheet is incorporated by reference herein, to the extent that the incorporated materials is not inconsistent herewith. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

In summary, numerous benefits have been described which result from employing the concepts described herein. The foregoing description of the one or more forms has been presented for purposes of illustration and description. It is not intended to be exhaustive or limiting to the precise form disclosed. Modifications or variations are possible in light of the above teachings. The one or more forms were chosen and described in order to illustrate principles and practical application to thereby enable one of ordinary skill in the art to utilize the various forms and with various modifications as are suited to the particular use contemplated. It is intended that the claims submitted herewith define the overall scope.

What is claimed is:

1. A needle guiding system, comprising:
   a compression sleeve;
   a guiding track configured to be attached to said compression sleeve, wherein said guiding track comprises:
      a first end;
      a second end; and
      a ramp comprising a sloped surface intermediate said first end and said second end; and
   a needle block assembly comprising:
      a body to be gripped by a user, and
      a needle;
   wherein said needle block assembly is movable in a first direction into engagement with said guiding track;
   wherein, upon engagement with said guiding track, said guiding track is structured to guide said needle block assembly along said sloped surface in a second direction toward said second end, wherein the second direction is different than the first direction;
   wherein said guiding track defines a fixed trajectory for said needle block assembly relative to a vein such that said needle is configured to enter the vein at a predetermined position and angle when said needle block assembly is seated in said second end of said guiding track, and wherein said fixed trajectory comprises a first angle and a second angle different from the first angle.

2. The needle guiding system of claim 1, wherein said guiding track further comprises a fluid valve.

3. The needle guiding system of claim 2, wherein said fluid valve is configured to be opened as a fluid bag is attached to said compression sleeve.

4. The needle guiding system of claim 3, further comprising said fluid bag, wherein said fluid bag comprises a first compartment and a second compartment.

5. The needle guiding system of claim 4, wherein said fluid bag is configured to store saline in said first compartment and medicament in said second compartment.

6. The needle guiding system of claim 1, wherein said guiding track further comprises a lock at said second end, wherein said lock is configured to engage said needle block assembly when said needle block assembly is seated in said second end of said guiding track.

7. The needle guiding system of claim 1, wherein said compression sleeve is configured to be positioned around a patient's arm in a position aligned with the predetermined position of the vein.

8. The needle guiding system of claim 1, wherein said compression sleeve comprises an insertion marker.

9. The needle guiding system of claim 1, wherein said compression sleeve comprises a flushing device.

10. The needle guiding system of claim 1, wherein said guiding track comprises an S-curve, wherein said needle block assembly is configured to travel along said S-curve in a distal direction.

11. The needle guiding system of claim 1, wherein said guiding track comprises rails, wherein said needle block assembly comprises pegs, and wherein said rails of said guiding track are configured to receive said pegs of said needle block assembly.

12. The needle guiding system of claim 1, wherein said needle is positioned on a bottom surface of said body of said needle block assembly, wherein said body of said needle block assembly is accessible by the user as said needle block assembly slides along said guiding track and said needle of said needle block assembly is retracted as said needle block assembly slides along said guiding track, wherein said guiding track defines an inflection intermediate said first angle and said second angle, and wherein said needle block assembly is slidable past said inflection.

13. The needle guiding system of claim 1, further comprising a sensor to monitor a status of the needle block assembly.

14. A mobile intravenous therapy device, comprising:
   a compression sleeve;
   a guiding track attached to said compression sleeve, wherein said guiding track comprises:
      a starting platform;
      a landing platform; and
      a slope between said starting platform and said landing platform;
   a fluid bag defining a fluid path threadably coupled to said guiding track, wherein said fluid bag comprises a medicament; and
   a needle assembly comprising:
      a body to be gripped by a user, and
      a needle;
   wherein said needle assembly is movable in a first direction into engagement with said guiding track;
   wherein, upon engagement with said guiding track, said guiding track is structured to guide said needle assembly in said guiding track from said starting platform to said landing platform along said slope in a second direction, wherein the second direction is different than the first direction;
   wherein said guiding track defines a fixed trajectory for said needle assembly relative to a vein such that said needle is configured to enter the vein at a predetermined position and angle once said needle assembly reaches said landing platform of said guiding track, and wherein said fixed trajectory comprises a first angle and a second angle different from the first angle.

15. The mobile intravenous therapy device of claim 14, wherein said fluid bag further comprises a saline solution.

16. The mobile intravenous therapy device of claim 14, wherein said needle further comprises a catheter extending out of said needle.

17. The mobile intravenous therapy device of claim 16, wherein said needle remains in said vein as said medicament is delivered intravenously through said catheter.

18. The mobile intravenous therapy device of claim 14, wherein said needle assembly further comprises a lock for securing said needle assembly at said landing platform of said guiding track.

19. The mobile intravenous therapy device of claim 18, wherein said lock comprises a tailhook.

20. The mobile intravenous therapy device of claim 18, wherein said lock comprises a snap fit engagement with said landing platform of said guiding track.

21. The mobile intravenous therapy device of claim 14, further comprising a plurality of indicators along a length of said guiding track.

22. The mobile intravenous therapy device of claim 14, wherein said compression sleeve is configured to be positioned around a patient's arm in a position aligned with the predetermined position of the vein.

23. The mobile intravenous therapy device of claim 14, wherein said needle is positioned on a bottom surface of said body of said needle assembly, wherein said body of said needle assembly is accessible by the user as said needle assembly slides along said guiding track and said needle of said needle assembly is retracted as said needle assembly slides along said guiding track.

24. The mobile intravenous therapy device of claim 14, further comprising a sensor to monitor a status of the needle assembly.

\* \* \* \* \*